(12) United States Patent
Fisker et al.

(10) Patent No.: US 10,595,973 B2
(45) Date of Patent: Mar. 24, 2020

(54) METHOD FOR DETERMINING RELATIVE ARRANGEMENT OF PATIENT'S JAWS

(71) Applicant: 3SHAPE A/S, Copenhagen K (DK)

(72) Inventors: Rune Fisker, Virum (DK); Birk Plönnigs, Frederiksberg (DK)

(73) Assignee: 3Shape A/S, Copenhagen K (DK)

( * ) Notice: Subject to any disclaimer, the term of this patent is extended or adjusted under 35 U.S.C. 154(b) by 0 days.

(21) Appl. No.: 15/557,383

(22) PCT Filed: Mar. 10, 2016

(86) PCT No.: PCT/EP2016/055137
§ 371 (c)(1),
(2) Date: Sep. 11, 2017

(87) PCT Pub. No.: WO2016/142470
PCT Pub. Date: Sep. 15, 2016

(65) Prior Publication Data
US 2018/0243057 A1    Aug. 30, 2018

(30) Foreign Application Priority Data
Mar. 10, 2015  (DK) .................. 2015 70135

(51) Int. Cl.
*A61C 13/097*   (2006.01)
*A61C 9/00*     (2006.01)
*A61C 19/05*    (2006.01)

(52) U.S. Cl.
CPC ............ *A61C 13/097* (2013.01); *A61C 9/004* (2013.01); *A61C 19/05* (2013.01)

(58) Field of Classification Search
CPC ... A61C 13/097; A61C 13/0004; A61C 1/084; A61C 9/004; A61C 11/00; A61C 19/05
See application file for complete search history.

(56) References Cited

U.S. PATENT DOCUMENTS 5,775,900 A * 7/1998 Ginsburg ........... A61C 13/0001
                                                    433/171
2010/0297581 A1* 11/2010 Wallace ............ A61C 13/0001
                                                    433/171
(Continued)

FOREIGN PATENT DOCUMENTS

WO    WO 2013/120955 A1    8/2013

OTHER PUBLICATIONS

International Search Report (PCT/ISA/210) dated Jun. 14, 2016, by the European Patent Office as the International Searching Authority for International Application No. PCT/EP2016/055137.
(Continued)

*Primary Examiner* — Cris L. Rodriguez
*Assistant Examiner* — Hao D Mai
(74) *Attorney, Agent, or Firm* — Buchanan Ingersoll & Rooney PC

(57) ABSTRACT

Disclosed is a method for scanning an edentulous patent who has a denture, where an impression material arranged at the gum-facing surfaces of the dentures is shaped by the patient's gums and both the teeth side and the gum-facing surface of the denture is scanned and the obtained digital 3D representations are used to determine the relative arrangement of the patient's edentulous jaws in a bite determined by the dentures.

11 Claims, 12 Drawing Sheets

(56) References Cited

U.S. PATENT DOCUMENTS

| | | |
|---|---|---|
| 2011/0060558 A1* | 3/2011 | Pettersson .......... A61B 17/8685 |
| | | 703/1 |
| 2011/0076159 A1 | 11/2011 | Chun et al. |
| 2012/0276502 A1 | 11/2012 | Marshall |
| 2013/0209962 A1* | 8/2013 | Thompson ............. A61C 13/01 |
| | | 433/191 |
| 2013/0218532 A1* | 8/2013 | Thompson ............. G06T 17/00 |
| | | 703/1 |
| 2014/0017634 A1 | 1/2014 | Kim |
| 2014/0255873 A1 | 9/2014 | Bullis et al. |
| 2015/0064644 A1* | 3/2015 | Scherer ................ A61C 9/0006 |
| | | 433/29 |
| 2015/0111177 A1* | 4/2015 | Fisker .................... A61C 13/01 |
| | | 433/196 |
| 2015/0272705 A1* | 10/2015 | Watson .................. A61C 1/084 |
| | | 433/173 |
| 2016/0278878 A1* | 9/2016 | Watson ................ A61C 9/0046 |
| 2016/0317264 A1* | 11/2016 | Derraugh ............... A61C 13/34 |

OTHER PUBLICATIONS

Written Opinion (PCT/ISA/237) dated Jun. 14, 2016, by the European Patent Office as the International Searching Authority for International Application No. PCT/EP2016/055137.

* cited by examiner

323

324

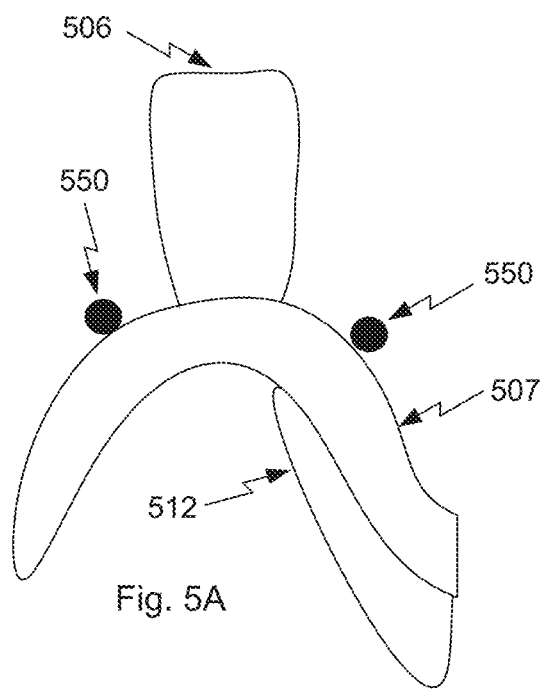
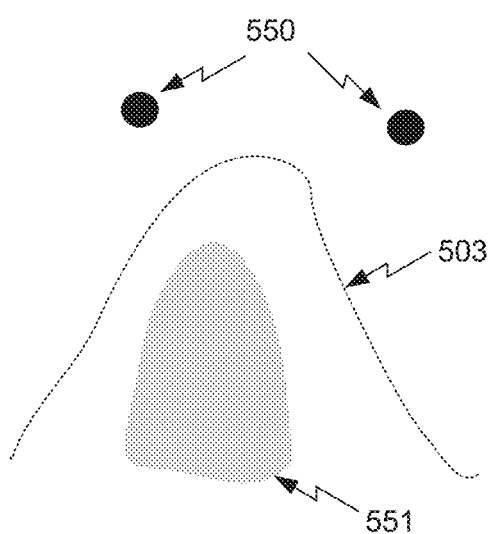
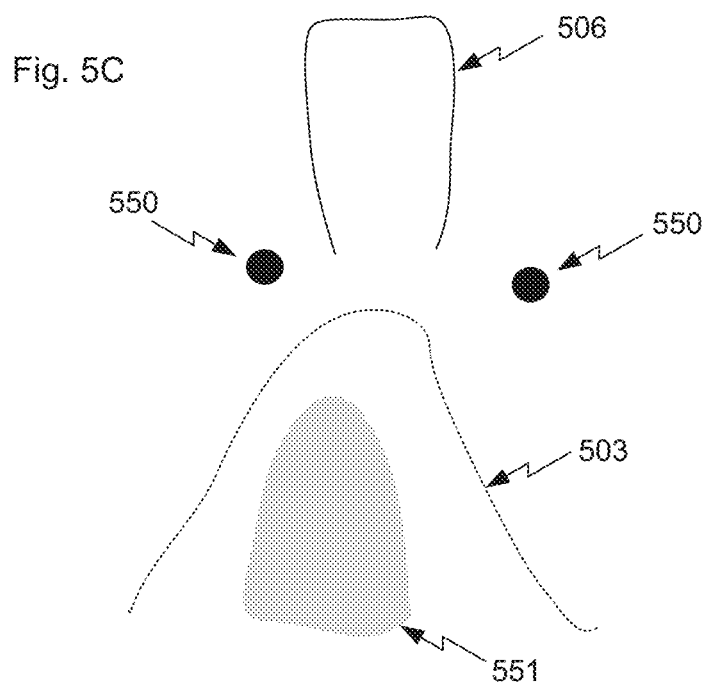

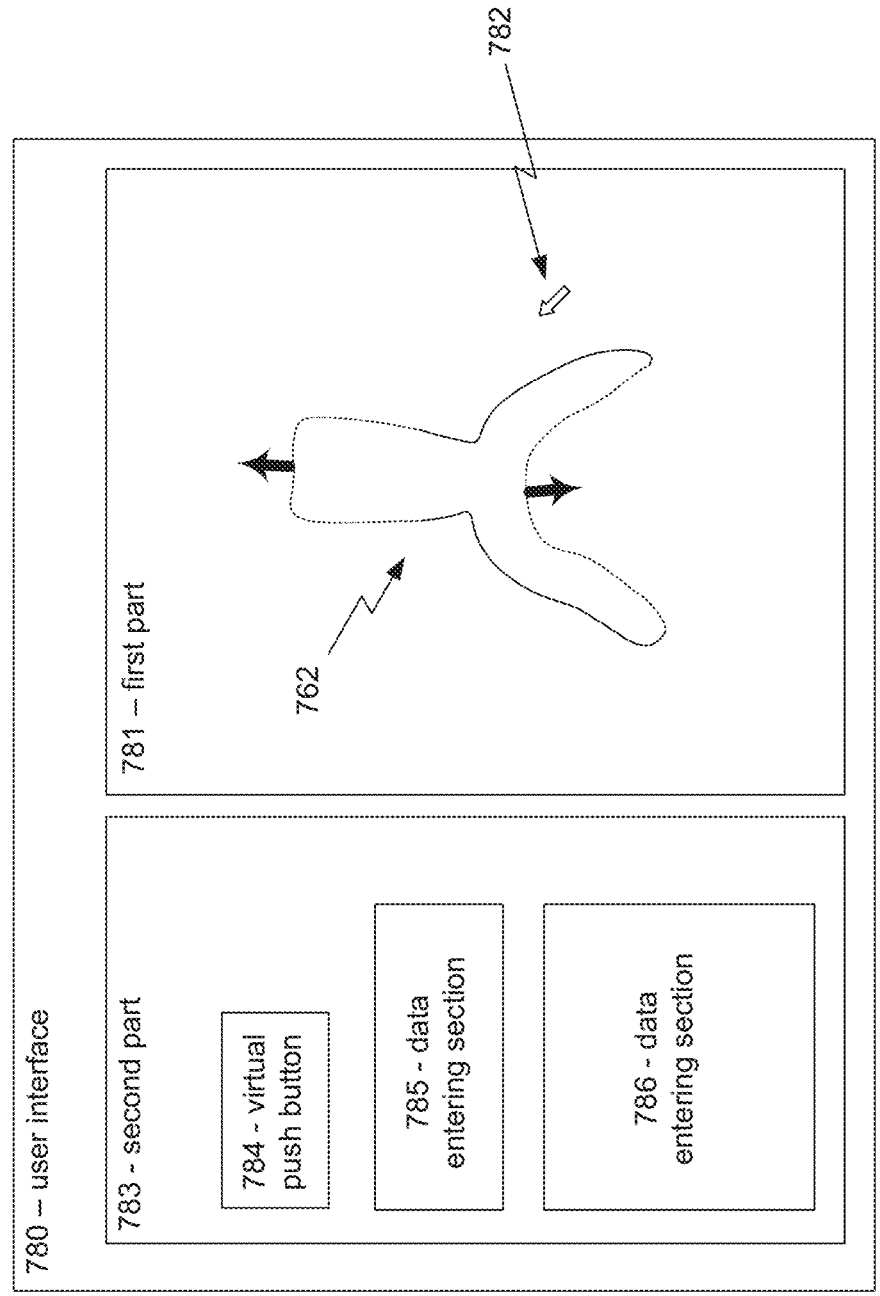

METHOD FOR DETERMINING RELATIVE ARRANGEMENT OF PATIENT'S JAWS

This invention generally relates to a method, user interface, a system and a computer program product for determining the relative arrangement of a patient's jaws in a bite position when the patient's occlusion at least partly is defined by the artificial teeth of a denture. More particularly, the invention relates to the use of an impression material on the backside of the denture for determining the relative arrangement of the gum surface and a surface of the opposing jaw.

BACKGROUND

For a patient having his natural teeth in both jaws the occlusion and the relative arrangement of the jaws in occlusion are defined by these teeth. Some patients are missing teeth to an extent where the occlusion no longer can be defined by the natural teeth alone. This is e.g. the case for a patient having at least one completely edentulous jaw. It may also be the case for a patient where some teeth are present but the antagonist teeth are not present.

A denture is a prosthetic device used for replacing teeth of an edentulous patient. The denture has a number of artificial denture teeth and a base part preferably shaped and colored to mimic the patient's gum to provide the most aesthetic appearance. The gum-facing surface of the base part of a conventional denture is configured for contacting the dental tissue of the jaw, i.e. the gum surface of the patient's alveolar ridge, in such a manner that the conventional denture is attached to the jaw by suction. Attaching by suction provides that the denture is removable but also that it may unintentionally release from the jaw. An alternative to a conventional denture is an implant-supported denture where the denture is fixated to the patient's jaw bone via implants secured in the jaw bone. This provides that the denture is held firmly in the correct position in the patient's mouth.

For a patient wearing a denture at a first one of the jaws, the occlusion can be defined by the denture teeth in collaboration with either teeth of a denture arranged at the opposing second one of the jaws or natural or implant supported teeth of the second one of the jaws. I.e. the natural, implant supported or artificial teeth of the second jaw acts as the antagonist teeth for the teeth of the denture in the first jaw.

The relative arrangement of an edentulous patient's jaws in a bite situation depends on the design of the denture. If e.g. the height of the denture teeth or denture base is increased, the corresponding jaw is moved further away from the occlusal plane and the other jaw.

When a patient has been wearing a conventional denture or a try-in denture for a while and has found that its design provides a good and pleasant jaw motion during a bite he may wish that the relative arrangement of the jaws in the denture defined occlusion is transferred to a new denture, such as to a new implant based denture.

Intra-oral scanning of e.g. a completely edentulous patient without the denture can provide digital 3D representations comprising surface data relating to the dental tissue in the patient's jaws. Arranging the denture in the mouth and scanning with the denture teeth in occlusion can provide a so-called bite scan which provides information relation to the relative arrangement of the first and second parts of the denture in occlusion. However this approach is not sufficient to provide information of the relative arrangement of the edentulous patient's jaws in the occlusion defined by the denture.

It thus remains a problem to provide a method for determining the relative arrangement of patient's jaws in a bite position when the patient's occlusion is not defined by the patient's natural teeth alone.

SUMMARY

The invention solves the abovementioned problem by arranging a layer of impression material on the gum-facing surface of the denture base and allowing the patient to bite while the denture is arranged at the corresponding jaw. The impression material is thus shaped according to the gum surface at the alveolar ridge and with the denture arranged according to the patient's bite. A digital 3D representation of the denture recorded with the gum shaped impression material at the backside provides information from which a digital 3D representation of the patient's gum surface can be derived. Further the geometrical data of the denture digital 3D representation relating to the artificial teeth can be used to establish a spatial correlation between the denture digital 3D representation and a bite scan comprising geometrical data for a surface of the opposing jaw. Thereby a link between the gum surface in the denture wearing jaw and a surface of the opposing jaw is established.

Disclosed is a method for determining the relative arrangement of a patient's first and second jaws in a bite position at least partly defined by a denture, the method comprising:
  obtaining a first digital 3D representation of a first denture for the first jaw, where the first digital 3D representation comprises geometrical data for the artificial teeth of the first denture and for the gum-facing surface of the denture base, where a first layer of impression material shaped according to the surface of the gum of the first jaw is arranged at the gum-facing surface;
  obtaining a second digital 3D representation comprising geometrical data for the artificial teeth of the first denture and geometrical data for antagonist teeth in the second jaw, where the artificial teeth of the first denture and the antagonist teeth are arranged according to the patient's occlusion;
  deriving from the first digital 3D representation a third digital 3D representation comprising geometrical data for the gum of the first jaw;
  obtaining a fourth digital 3D representation comprising geometrical data for a surface of the second jaw; and
  determining the relative arrangement of the first and second jaws in the bite position based on the geometrical data of the first, second, third and fourth digital 3D representations.

In the context of the present invention the phrase "the bite position" refers to the situation where the patient's jaws are in the position where the artificial teeth of the (first) denture is in occlusion with the antagonist teeth.

In the context of the present invention the phrase "antagonist teeth" refers to natural teeth or artificial teeth of the jaw opposite to the (first) denture. The artificial teeth may e.g. be the teeth of a second denture arranged at the opposite jaw or implant supported teeth in the second jaw.

In the context of the present invention an impression material is a material which can be shaped according e.g. to the shape of the patient's gums when arranged in contact with the gum and which maintains its shape when removed from the gum. Several impression materials such as elastomers, polysulfides, polyethers and silicones are known to the skilled person.

Placing the first denture at the gum surface of the alveolar ridge of the first jaw and bringing the upper and lower jaw into their relative position during the occlusion of the first denture and the antagonist teeth provides that the layer of impression material, e.g. a silicone material, is shaped according to the gum profile.

Often there is a discrepancy between the gum-facing side of a denture and the profile of the gum, such that at some places there is a gap between the gum-facing surface of the denture and the gum surface. Scanning a denture without impression material formed according to the gum profile will thus result in a less accurate determining of the relative arrangement of the gums in an occlusion determined at least partly by a denture.

The first layer of the impression material is arranged at a gum-facing surface of the denture base, such that when the denture is arranged at the patient's gum, the impression material is shaped according to the gum profile of the first jaw.

In the following is described how a digital 3D representation of the denture comprising geometric data for both part of the denture teeth and for the gum-shaped impression material can be used for determining the relative arrangement of the gum and a surface of the opposing jaw. The surface of the opposing jaw can be that of existing teeth in the opposing jaw or of the gum in cases where both jaws are at least partly edentulous.

The first digital 3D representation has geometrical data for the layer of impression material arranged on the gum-facing surface of the denture base. In some areas of the gum-facing surface of the denture base is in contact with the gum surface when the denture is arranged on the alveolar ridge. The portion of the digital 3D representation relating to the gum-facing surface may thus have geometrical data relating to both the impression material and the gum-facing surface of the denture base.

The second digital 3D representation is recorded with the artificial teeth of the first denture and the antagonist teeth arranged in occlusion such that this digital 3D representation comprises geometrical data for the labial/buccal surfaces of these teeth where the geometrical data in the second digital 3D representation express the relative arrangement of the denture teeth in the first jaw and the teeth at the second jaw in the patient's bite.

The second digital 3D representation is also known to the skilled person as a bite scan in which the two jaws are arranged according to the occlusion, i.e. with the artificial teeth of the first denture arranged in occlusion with the antagonist teeth. The second digital 3D representation comprises geometrical data expressing the shape of the artificial teeth of the first denture and geometrical data expressing the shape of antagonist teeth of the opposing second jaw obtained while the jaws are in occlusion. The second digital 3D representation thus provides information about the relative arrangement of the artificial teeth of the first denture and the antagonist in occlusion. The spatial correlation between digital 3D representations with geometrical data for surfaces in the patient's upper and lower jaw can thus be established by correlating each of these digital 3D representations with or via the bite scan.

In some embodiments, the third digital 3D representation is derived from the portion of the first digital 3D representation relating to the gum-facing surface of the first denture with the first layer of impression material. Since the first digital 3D representation express the shape of the denture, the surface generated e.g. by selecting the appropriate geometrical data of the first digital 3D representation initially has the wrong sidedness for it to truly express the shape of the patient's gum. The method hence preferably comprises inverting the surface normal of the surface generated from the first digital 3D representation such that the derived third digital 3D representation express the shape of the gum in the patient's first jaw. I.e. the third digital 3D representation provides a positive representation of the gum surface at the alveolar ridge of the first jaw.

Given that the third digital 3D representation is derived from the first digital 3D representation, the spatial correlation between the third and fourth digital 3D representations is also determined when the spatial correlation between the first and fourth digital 3D representations is known.

In some embodiments, deriving the third digital 3D representation comprises selecting the portion of the geometrical data of the first digital 3D representation relating to the gum-facing surface of the denture base and inverting the surface normal of the surface defined by the selected portion.

In some embodiments, the determining comprises selecting and/or identifying the portion of the geometrical data of the first digital 3D representation relating to the gum-facing surface. Since the gum-facing surface of the denture base with the impression material is shaped according to the surface of the gum the corresponding geometrical data also relates to the shape of the gums. However, since the gum-facing surface of the denture base provides a negative of the gum surface, the determining in some embodiments comprises inverting the surface normal for the surface defined by the portion of the geometrical data of the first digital 3D representation relating to the gum-facing surface. A third digital 3D representation generated from the identified and inverted geometrical data will accordingly will provide a positive representation of the gum surface having a surface normal with the correct direction.

The third digital 3D representation can be identified as a selected region of the first digital 3D representation after the relative arrangement of the first and fourth digital 3D representations has been determined. The relative arrangement of the selected region, and thus of the third digital 3D representation, relative to the fourth digital 3D representation is then already determined. When the patient has this natural teeth in the second jaw and the fourth digital 3D representation comprises geometrical data for these natural teeth, the relative arrangement of the first jaw (expressed by the third digital 3D representation) and the second jaw (expressed by the fourth digital 3D representation) is then determined.

In some embodiments, the third or fourth digital 3D representation comprises geometrical data for the alveolar ridge and/or the palatine rugae of the patient's upper jaw.

In some embodiments, a sixth digital 3D representation comprising geometrical data for the alveolar ridge and/or the palatine rugae is obtained and the method comprises determining one or more transformations for mapping the sixth digital 3D representation into the coordinate system of the first, second or fourth digital 3D representation.

The geometrical data relating to the palatine rugae can be taken into account in designing a new denture for the patient where the new denture mimics the patient's on rugae.

When two digital 3D representations are aligned based on geometrical data corresponding to the same surface or surfaces the two digital 3D representations can be said to be mapped into the same coordinate system. For example the geometrical data relating to the artificial teeth of a denture found in the first and the second digital 3D representations can be used for aligning these two digital 3D representations. When two or more digital 3D representations are aligned or mapped into the same coordinate system the geometrical data of the digital 3D representations are arranged according to the relative arrangement of the corresponding physical surfaces in the patient's mouth. The transformations configured for providing such alignment or mapping may be in the form of transformation matrices.

The method utilizes that the second digital 3D representation, i.e. the bite scan, comprises geometrical data for both the artificial teeth of the denture in the first jaw and the antagonist teeth of the second jaw with the artificial and antagonist teeth arranged according to the patient's bite. The first and the fourth digital 3D representations comprising geometrical data for the artificial teeth and antagonist teeth, respectively, can thus be linked via the second digital 3D representation.

In some embodiments, determining the relative arrangement comprises deriving one or more transformations for mapping the third and fourth digital 3D representations into the same coordinate system. The one or more transformations establish the spatial correlation between the third and fourth digital 3D representations.

When the fourth digital 3D representation comprises geometrical data for natural teeth of the second jaw this provides that the geometrical data for the gum surface of the first jaw (the third digital 3D representation) is mapped into the same coordinate system as the natural teeth of the second jaw (the fourth digital 3D representation), i.e. the relative arrangement of these natural teeth and the gum surface in the first jaw is then determined.

The transformations for mapping of the third and fourth digital 3D representations into the same coordinate system may be determined based on transformations for mapping the first and the fourth digital 3D representation into the same coordinate system as the second digital 3D representation such that the second digital 3D representation provides a link between the geometrical data for the two jaws.

The alignment of the digital 3D representations is preferably based on the geometrical data corresponding to the same surface or surfaces. For example the portion of the fourth digital 3D representation corresponding to a given artificial tooth can be aligned with the corresponding tooth surface in second digital 3D representation. The alignment can be realized by using a computer implemented Iterative Closest Point algorithm applied to the corresponding portions of the two digital 3D representations such that these portions of the digital 3D representations are aligned.

In some embodiments, the one or more transformations provide a mapping of the first and second digital 3D representations into the same coordinate system at least partly based on the geometrical data for the artificial teeth in the first digital 3D representation and the corresponding part of the geometrical data of the second digital 3D representation.

In some embodiments, determining the relative arrangement comprises mapping or deriving one or more transformations for mapping the first and second digital 3D representations into the same coordinate system. This can be done at least partly based on the geometrical data of the artificial teeth in the first digital 3D representation and the corresponding geometrical data of the second digital 3D representation.

The one or more transformations are configured to provide that in the common coordinate system, the geometrical data for the artificial teeth in the first digital 3D representation is aligned with the geometrical data for the artificial teeth in the second digital 3D representation. The geometrical data of the first digital 3D representation relating to the gum surface of the first jaw are then expressed in the same coordinate system as the geometrical data for the antagonist teeth in the second digital 3D representation.

As also stated above, the antagonist teeth can be natural teeth of the jaw opposite to the first denture, i.e. when the denture is for the upper jaw the antagonist teeth are the natural teeth of the lower jaw, or vice versa.

In some embodiments, the antagonist teeth comprises natural teeth of the second jaw and at least part of the geometrical data comprised in the fourth digital 3D representation relates to a surface of the natural teeth of the second jaw, and where the relative arrangement of the gum of the first jaw and the natural teeth of the second jaw is determined at least partly by establishing a spatial correlation between the third and fourth digital 3D representations.

In some embodiments, the antagonist teeth of the opposing second jaw comprises natural teeth and the method comprises obtaining a fourth digital 3D representation comprising geometrical data expressing the shape of the natural teeth, and where the relative arrangement of a patient's jaws in the bite position is determined based on the first, second, third, and fourth digital 3D representations.

Disclosed is a method for determining the relative arrangement of a patient's first and second jaws in a bite position defined by a denture in the patient's first jaw and teeth of the second jaw, the method comprising:

obtaining a first digital 3D representation of the denture, the first digital 3D representation comprising geometrical data for the artificial teeth of the denture and for the gum-facing surface of the denture base, where a layer of impression material shaped according to the surface of the gum of the first jaw is arranged at the gum-facing surface of the denture base;

obtaining a second digital 3D representation comprising geometrical data for the artificial teeth of the first denture and geometrical data for antagonist teeth in the second jaw, where the artificial teeth of the first denture and the antagonist teeth are arranged according to the patient's occlusion;

deriving from the first digital 3D representation a third digital 3D representation comprising geometrical data for the gum of the first jaw;

obtaining a fourth digital 3D representation comprising geometrical data for the teeth of the second jaw; and determining the spatial correlation between the first and fourth digital 3D representations by aligning or deriving transformations for aligning the first and fourth digital 3D representations with the second digital 3D representation.

The third digital 3D representation provides a positive representation of the gum surface at the alveolar ridge of the first jaw. Given that the third digital 3D representation is derived from the first digital 3D representation, the spatial correlation between the third and fourth digital 3D representations is also determined once the spatial correlation between the first and fourth digital 3D representations is known. Applying the transformation for aligning the first and second digital 3D representations to the third digital 3D representation provides that the geometrical data of the third and the fourth digital 3D representations are spatially correlated, such as expressed in the same coordinate system. Thereby the relative arrangement of the patient's first and second jaws in the bite position defined by the denture and the teeth of the second jaw has been determined based on the geometrical data of the first, second, third and fourth digital 3D representations.

As also stated above, the antagonist teeth may comprise artificial teeth of a second denture arranged at the patient's second jaw patient's opposing the first jaw where the second denture comprises artificial teeth and a denture base comprising a gum-facing surface at which a second layer of impression material is arranged, where the second layer of impression material is shaped according to the gum of the second jaw.

Similar to the first denture, the second denture is placed at the gum (alveolar ridge) of the second jaw prior to the scanning of the second denture and the dentist confirms that the first and second dentures are arranged according to a satisfactory/desired occlusion. Thereby the layer of impression material, e.g. a silicone material, at the gum-facing surface of the base of the second denture is shaped according to the profile of the second gum.

When the patient has dentures in both the first and second jaws, the fourth digital 3D representation comprises geometrical data for the gum of the second jaw.

Thus in some embodiments, the method comprises obtaining a fifth digital 3D representation provided by 3D scanning at least part of the second denture with the denture base comprising a gum-facing surface at which the second layer of impression material is arranged where the second layer of impression material is shaped according to the gum of the second jaw, and where the fifth digital 3D representation comprises geometrical data for the surface of the artificial teeth of the second denture and for the gum-facing surface with the second layer of impression material. The fourth digital 3D representation can then be derived from a part of the geometrical data of the fifth digital 3D representation relating to the gum-facing surface of the second denture with the second layer of impression material. The relative arrangement of the gum of the first jaw and the gum of the second jaw may then be determined at least partly by establishing a spatial correlation between the third and fourth digital 3D representations. In order to express the shape of the gum in the second jaw, the surface forming by the selected geometrical data of the fifth digital 3D representation must be inverted similar to what is described above in relation to the third digital 3D representation to provide that the fourth digital 3D representation gives a positive representation of the gum in the second jaw.

The fourth digital 3D representation can be identified as a selected region of the fifth digital 3D representation after the relative arrangement of the fifth and the first or third digital 3D representations has been determined. The relative arrangement of the selected region, and thus of the fourth digital 3D representation, relative to the first or second digital 3D representation is then already determined. The relative arrangement of the first jaw and second jaw expressed by the third and fourth digital 3D representations, respectively, is then determined.

In some embodiments, the one or more transformations provide a mapping of the second and fifth digital 3D representations into the same coordinate system at least partly based on the geometrical data for the artificial teeth in the fifth digital 3D representation and the corresponding part of the geometrical data of the second digital 3D representation.

In some embodiments, the one or more transformations provide a mapping of the second and fourth digital 3D representations into the same coordinate system at least partly based on the geometrical data for the natural teeth of the second jaw in the fourth digital 3D representation and the corresponding part of the geometrical data of the second digital 3D representation.

The second digital 3D representation is the one providing the link between the upper and lower jaw and their teeth (artificial and/or natural) and gums. It is hence advantageous to determine the transformation matrices for mapping the other digital 3D representations into the coordinate system of the second digital 3D representation.

For a patient having a denture in both the upper and lower jaw, the transformations which map the first and fifth digital 3D representations into the coordinate system of the second digital 3D representation can also be used to map the third and fourth digital 3D representations of the gums in the first and second jaws into the same coordinate system. This provides that the relative arrangement of the upper and lower jaw is determined.

For a patient having a denture in the first jaw and natural teeth in the second jaw, the transformation which maps the first digital 3D representation into the coordinate system of the second digital 3D representation can also be used to map the third digital 3D representation of the gums in the first jaw into the same coordinate system. When a transformation for mapping the fourth digital 3D representation into the coordinate system of the second digital 3D representation also is determined, the transformations required for bringing the geometrical data for the gum in the first jaw into the same coordinate system of the natural teeth of the second jaw has been determined. This provides that the relative arrangement of the upper and lower jaw is determined.

Disclosed is a method for determining the relative arrangement of artificial teeth of a denture and the gum surface at the patient's alveolar ridge where the denture is arranged, wherein the method comprises:
  obtaining a first digital 3D representation comprising geometrical data for one or more artificial teeth of the denture and geometrical data for the gum-facing surface of the denture base, where the geometrical data for the gum-facing surface comprises geometrical data for a layer of an impression material shaped according to the gum surface at the alveolar ridge; and
  generating a third digital 3D representation by selecting from the first digital 3D representation geometrical data relating to the gum-facing surface of the denture base and inverting the surface normal for the surface defined by the geometrical data such that the third digital 3D representation provides a positive representation of the gum surface.

In some embodiments, the method comprises identifying a portion of the geometrical data of the first digital 3D representation which relate to the one or more artificial teeth.

In some embodiments, a third digital 3D representation comprising geometrical data expressing the shape of the gum surface is generated at least partly by selecting a portion of the gum-facing surface in the first digital 3D representation and inverting the surface formed by the selected geometrical data.

Since the portion of the geometrical data of the first digital 3D representation relating to the one or more artificial teeth and the third digital 3D representation are inherently linked the relative arrangement of at least one surface of the artificial teeth and the gum surface is determined. Further, the first and the third digital 3D representations can directly be expressed in the same coordinate system according to the relative arrangement of the tooth and gum surfaces in the patient's mouth.

The use of an impression material at the gum-facing surface of the denture base provides the advantage that the correct shape and the correct position relative to the patient's gum can be determined. If the impression material is not applied to the denture backside and shaped according to the gum, there is an uncertainty in the relative position and shape since the denture base does not exactly follow the surface of the gum. Scanning the denture backside without the use of the impression material to capture the gum shape and position this method is inaccurate The method can be applied for both the upper and lower jaw of the patient is edentulous in both jaws, such that the relative arrangement of the gum surfaces relative to denture teeth surfaces are determined for both the upper and the lower jaw. The derived gum surfaces of the upper and lower jaws can then be correlated using a bite scan, i.e. a second digital 3D representation recorded while the patient bites, i.e. while the artificial teeth of the upper and lower dentures are arranged in occlusion. Aligning or determining transformations for aligning the geometrical data of the digital 3D representations for the upper and lower dentures with the corresponding tooth surfaces of the bite scan then provides that the spatial correlation between the gum surfaces in the upper and lower jaws is determined for the denture defined bite.

Disclosed is a method for determining the relative arrangement of the surface of teeth in a denture and the surface of the alveolar ridge in the jaw where the denture is arranged, the method comprising:
  obtaining a denture comprising a denture base and denture teeth, where the denture base comprises a gum-facing surface at which a layer of an impression material is arranged,
  arranging the denture at the corresponding jaw according to the patient's occlusion while wearing the denture, such that the layer of impression material is shaped according to the alveolar ridge of the jaw;
  obtaining a digital 3D representation by 3D scanning at least part of the denture teeth surface and at least part of the impression material shaped by the alveolar ridge; and
  deriving the relative arrangement of the denture tooth surface and the alveolar ridge surface from the obtained digital 3D representation.

Disclosed is a system for determining the relative arrangement of a patient's first and second jaws in a bite position at least partly defined by a denture, wherein the system comprises a data processing unit and a non-transitory computer readable medium encoded with a computer program product providing a digital tool for determining the relative arrangement of the jaws by a method comprising:
  obtaining a first digital 3D representation of a first denture for the first jaw, where the first digital 3D representation comprises geometrical data for the artificial teeth of the first denture and for the gum-facing surface of the denture base, where a first layer of impression material shaped according to the surface of the gum of the first jaw is arranged at the gum-facing surface;
  obtaining a second digital 3D representation comprising geometrical data for the artificial teeth of the first denture and geometrical data for antagonist teeth in the second jaw, where the artificial teeth of the first denture and the antagonist teeth are arranged according to the patient's occlusion;
  deriving from the first digital 3D representation a third digital 3D representation comprising geometrical data for the gum of the first jaw;
  obtaining a fourth digital 3D representation comprising geometrical data for a surface of the second jaw; and
  determining the relative arrangement of the first and second jaws in the bite position based on the geometrical data of the first, second, third and fourth digital 3D representations.

Disclosed is a system for determining the relative arrangement of a patient's first and second jaws in a bite position at least partly defined by a denture, wherein the system comprises a data processing unit and a non-transitory computer readable medium encoded with a computer program product providing a digital tool for determining the relative arrangement of a patient's first and second jaws in a bite position at least partly defined by a denture, wherein the system is configured for loading into the computer readable medium a first digital 3D representation of a first denture for the first jaw, where the first digital 3D representation comprises geometrical data for the artificial teeth of the first denture and for the gum-facing surface of the denture base, where a first layer of impression material shaped according to the surface of the gum of the first jaw is arranged at the gum-facing surface, and a second digital 3D representation comprising geometrical data for the artificial teeth of the first denture and geometrical data for antagonist teeth in the second jaw, where the artificial teeth of the first denture and the antagonist teeth are arranged according to the patient's occlusion, and where the computer program product is configured for deriving from the first digital 3D representation a third digital 3D representation comprising geometrical data for the gum of the first jaw when program code of the computer program product are executed on the data processing unit.

In some embodiments the system is configured for loading into the computer readable medium a fourth digital 3D representation comprising geometrical data for a surface of the second jaw from a fifth digital 3D representation loaded into the computer readable medium.

In some embodiments the computer program product is configured for deriving a fourth digital 3D representation comprising geometrical data for a surface of the second jaw from a fifth digital 3D representation loaded into the computer readable medium.

In some embodiments the computer program product is configured for determining the relative arrangement of the first and second jaws in the bite position based on the geometrical data of the first, second, third and fourth digital 3D representations.

Furthermore, the invention relates to a computer program product comprising program code means for causing a data processing system to perform the method according to any of the embodiments when said program code means are executed on the data processing system.

Disclosed is a non-transitory computer readable medium encoded with a computer program product providing a graphical user interface for determining the relative arrangement of a patient's first and second jaws in a bite position at least partly defined by a denture by a method comprising:
  obtaining a first digital 3D representation of a first denture for the first jaw, where the first digital 3D representation comprises geometrical data for the artificial teeth of the first denture and for the gum-facing surface of the denture base, where a first layer of impression material shaped according to the surface of the gum of the first jaw is arranged at the gum-facing surface;
  obtaining a second digital 3D representation comprising geometrical data for the artificial teeth of the first denture and geometrical data for antagonist teeth in the second jaw, where the artificial teeth of the first denture and the antagonist teeth are arranged according to the patient's occlusion;

deriving from the first digital 3D representation a third digital 3D representation comprising geometrical data for the gum of the first jaw;

obtaining a fourth digital 3D representation comprising geometrical data for a surface of the second jaw; and determining the relative arrangement of the first and second jaws in the bite position based on the geometrical data of the first, second, third and fourth digital 3D representations.

The first digital 3D representation comprising geometrical data for the patient's gum in one of the jaws can be used in designing a surgical guide configured for assisting a dentist in drilling implant holes into the patient's jaw bone. Knowledge of the position and quality of the patient's jaw bone is also needed to design the drill guide. Such data can be in the form of an X-ray image obtained by X-ray scanning, such as by Cone Beam Computer Tomography, where the bone density in the different parts of the jaw bone is detected. In order to be able to bring the jaw bone data acquired by the X-ray scanning and the geometrical data for the gum surface of the same jaw into the same coordinate system, radiopaque fiducial markers can be arranged on the denture. The fiducial markers will then appear both in the first digital 3D representation and in the X-ray image such that the first digital 3D representation and the X-ray image can be brought into the same coordinate system by aligning the fiducial marker data. When the drill guide is for the second jaw, the fifth digital 3D representation is aligned with the bone data from the X-ray scan.

When the surface data of the digital 3D representation and the X-ray data are expressed in the same coordinate system, the position of the bone relative to the gum surface is determined and a digital drill guide design can be generated from which design a the drill guide can be manufactured.

In some embodiments, a digital drill guide design is generated for the first jaw based on the first digital 3D representation and an obtained X-ray image describing the bone of the first jaw, wherein the method comprises generating a digital drill guide body from a portion of the first digital 3D representation comprising geometrical data for the gum-facing surface with the first layer of impression material and subtracting from the digital drill guide body one or more CAD models of inserts for guide tubes shaped to assist a drill in drilling implant holes into the patient's jaw.

The drill guide body is configured for resting on the patient's gum at the alveolar ridge. The inserts defined in the drill guide body can support one or more guide tubes configured for guiding the drill used for removal of bone material to make space for the implant.

In some embodiments, generating the digital drill guide design comprises using a portion of the first digital 3D representation to shape at least the gum-facing part of the digital drill guide design. This can e.g. be done by replacing the part of the first digital 3D representation relating to the artificial teeth with a surface which follows the shape of the denture base. This can be done by detecting the margin line for the artificial teeth of the first denture, i.e. the line where the denture base contacts the artificial teeth of the denture, digitally deleting the portion of the first digital 3D representation relating to the artificial teeth, and generating a surface which closes the hole formed where the deleting portion was located, where the generated surface follows the shape of the denture base. One or more CAD models of the tubes used for guiding the surgical drill are then arranged relative to the remaining denture base portion of the first digital 3D representation based on the knowledge of the patient's bone expressed by the X-ray scan. When the tube CAD models have been placed a connecting surface bridging the denture base portion of the first digital 3D representation and the tube CAD models is generated e.g. by applying a loofting algorithm.

The digital drill guide design can also be generated from the third digital 3D representation or sixth digital 3D representation which both express the shape of the gum for which the drill guide is designed. The drill guide body can then be generated by a shelling of the third, fourth or sixth digital 3D representation.

The advantage of using a denture with a layer of impression material on the gum-facing surface is that an accurate representation of the patient's gum is provided where the position of the gum surface relative to the patient's jaw bone is known with a good precision. This provides that the drill guide when arranged on the gum surface is located exactly according to the relative position which was used when determining the position of the insert of the guide tubes. When the drill guide position on the gum is accurate and known with high precision the drilling into the jaw bone is precise.

Disclosed is a method for generating a digital drill guide design from which at least the body of a drill guide can be manufactured by direct digital manufacture, wherein the method comprises:

obtaining a digital 3D representation comprising geometrical data for artificial teeth of a denture, for a layer of an impression material arranged on the gum-facing surface of the denture base where the layer of impression material is shaped according to the gum in the alveolar ridge, and for one or more fiducial markers arranged at the denture;

obtaining a X-ray scan comprising data for the bone structure of the jaw and data for the fiducial markers, where the X-ray scan is recorded with the denture arranged at the patient's gum surface according to the patient's bite;

aligning the digital 3D representation and the X-ray scan based on the data for the fiducial markers;

deriving the relative position of the gum surface and the jaw bone from the aligned digital 3D representation and X-ray scan;

planning the location of one or more implants in the patient's jaw bone;

generating the body of the digital drill guide design at least partly based on the geometrical data of the digital 3D representation relating to the gum-facing surface; and defining apertures for drill guide tube inserts in the body based on the planned implant position and the derived relative arrangement of the bone structure and the gum surface.

The alignment of the geometrical data of the digital 3D representation and the X-ray scan provide that a transformation for expressing the two data set in the same coordinate system is determined.

In some embodiments, the method comprises identifying the portion of the geometrical data of the digital 3D representation which relate to the gum-facing surface of the denture base and deriving geometrical data for the gum surface from this portion. The geometrical data for the gum surface can be provided in the form of a separate digital 3D representation. Since the geometrical data for the gum surface are derived from the digital 3D representation of the denture these geometrical data are correlated with the geometrical data for the fiducial markers and the same transformation which brings the digital 3D representation and the X-ray scan into the same coordinate system can also be applied to bring the gum surface digital 3D representation into the same coordinate system as the X-ray scan. The relative position of the gum surface and the jaw bone is then determined.

In some embodiments, the vertical separation from the jaw bone to the occlusal surface of the artificial teeth is determined based on the digital 3D representation and the X-ray data. When the digital 3D representation and the X-ray data are expressed in the same coordinate system, the vertical distance can readily be determined. It is advantageous to know the vertical distances for the upper and lower jaw when designing a new denture for the patient. If the bone of one jaw has retracted it may be necessary to introduce an additional supporting structure to obtain a functionally and aesthetic pleasing denture.

In some embodiments, the method comprises identifying the portion of the geometrical data of the digital 3D representation relating to the surface of the artificial teeth of the denture. For the same reasons why the geometrical data of the digital 3D representation relating to the gum-facing surface are spatially correlated with the data of the X-ray scan the geometrical data relating to the artificial teeth surface are also correlated with the X-ray data when the X-ray scan and the digital 3D representation are aligned. The geometrical data for the surface of the artificial teeth is hence correlated with the X-ray data relating to the jaw bone. In some embodiments, planning the location of the one or more implants in the patient's jaw bone is based on the position of the artificial teeth relative to the jaw bone where the planned positions aim at providing that the implants will provide good support for an implant supported denture which has substantially the same tooth setup as the existing denture. In some embodiments the longitudinal axis of an implant in a planned position in the upper jaw is slightly inclined towards the patent's median plane. In some embodiments the longitudinal axis of an implant in a planned position in the lower jaw is slightly inclined away from the median plane. This is advantageous when the patient with age experiences that the upper jaw expands while the lower jaw becomes mores narrow since its provide that the implants will provide a better support for the denture. If the patient's is pleased with the setup of teeth in his current denture the implants should preferably provide good support for a denture with such a setup in spite of the expansion/shrinking of the upper/lower jaw. The abovementioned inclinations of the implants can provide this.

In some embodiments, the location of the implants in the jaw bone is planned based on the relative position of the jaw bone and the surface of the artificial teeth. The relative position of the gum surface and the jaw bone being derived from the aligned digital 3D representation and X-ray scan.

In some embodiments, the guide tube inserts can be generated by Boolean subtraction of a digital structure representing the insert which will be introduced in the drill guide body.

The present invention relates to different aspects including the method described above and in the following, and corresponding methods, each yielding one or more of the benefits and advantages described herein, and each having one or more embodiments corresponding to the described embodiments and/or disclosed in the appended claims.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIGS. 5A-5F illustrate design of a drill guide body.

FIG. 7 illustrates a user interface.

DETAILED DESCRIPTION

In the following description, reference is made to the accompanying figures, which show by way of illustration how the invention may be practiced.

FIG. 1 show dentures for a patient's upper and lower jaw.

Figure 1A:
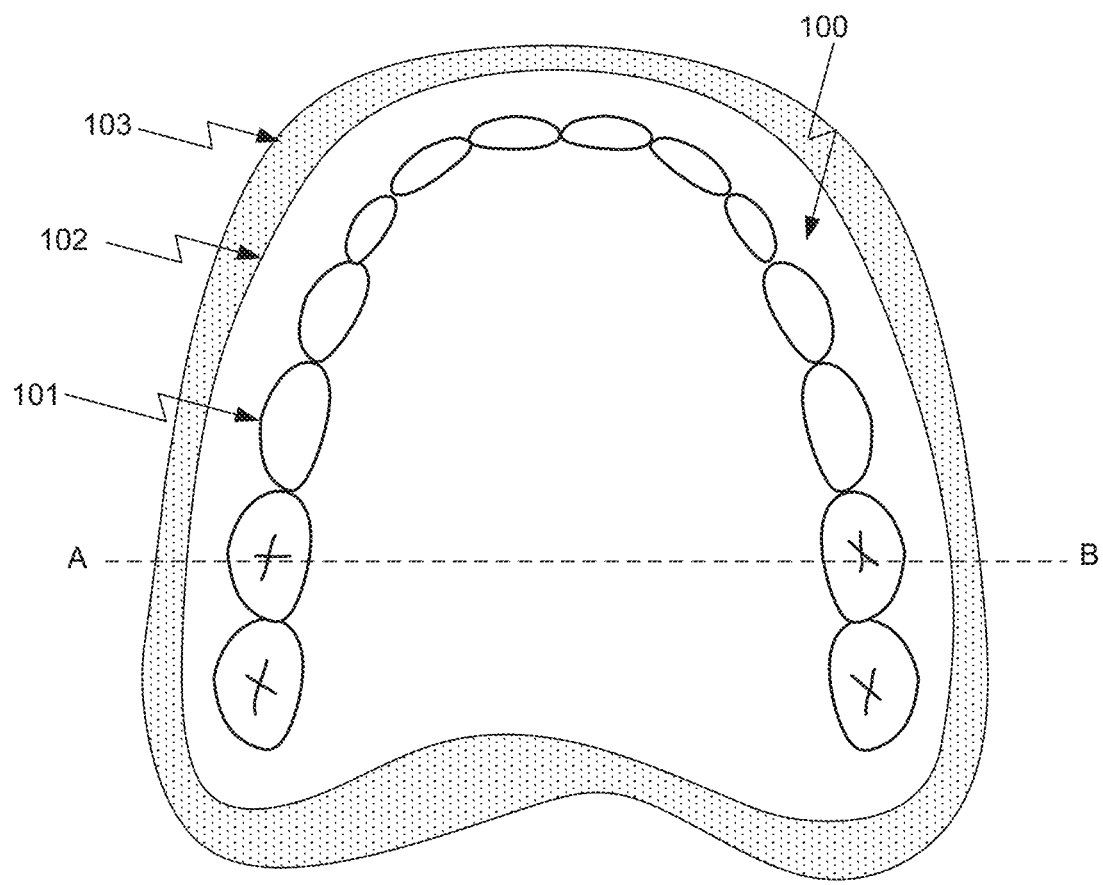
FIGS. 1A-1D show dentures for a patient's upper and lower jaw.

FIG. 1A shows a schematic of a maxillary denture 100, i.e. a denture for the patient's upper jaw viewed from the patient's occlusal plane. The artificial teeth 101 of the maxillary denture 100 are secured in the denture base 102 which contacts the patient's gums 103 in the patient's mouth. The illustrated denture is for a completely edentulous upper jaw and the artificial teeth 101 define the occlusion in collaboration with antagonist teeth of the lower jaw. The antagonist teeth can be the patient's natural teeth when these are present or the teeth of mandibular denture arranged at the lower jaw.

Figure 1B:
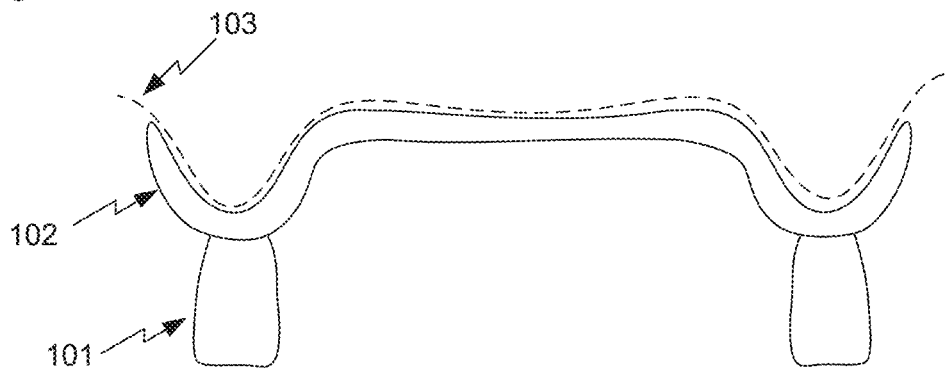
Figure 1C:
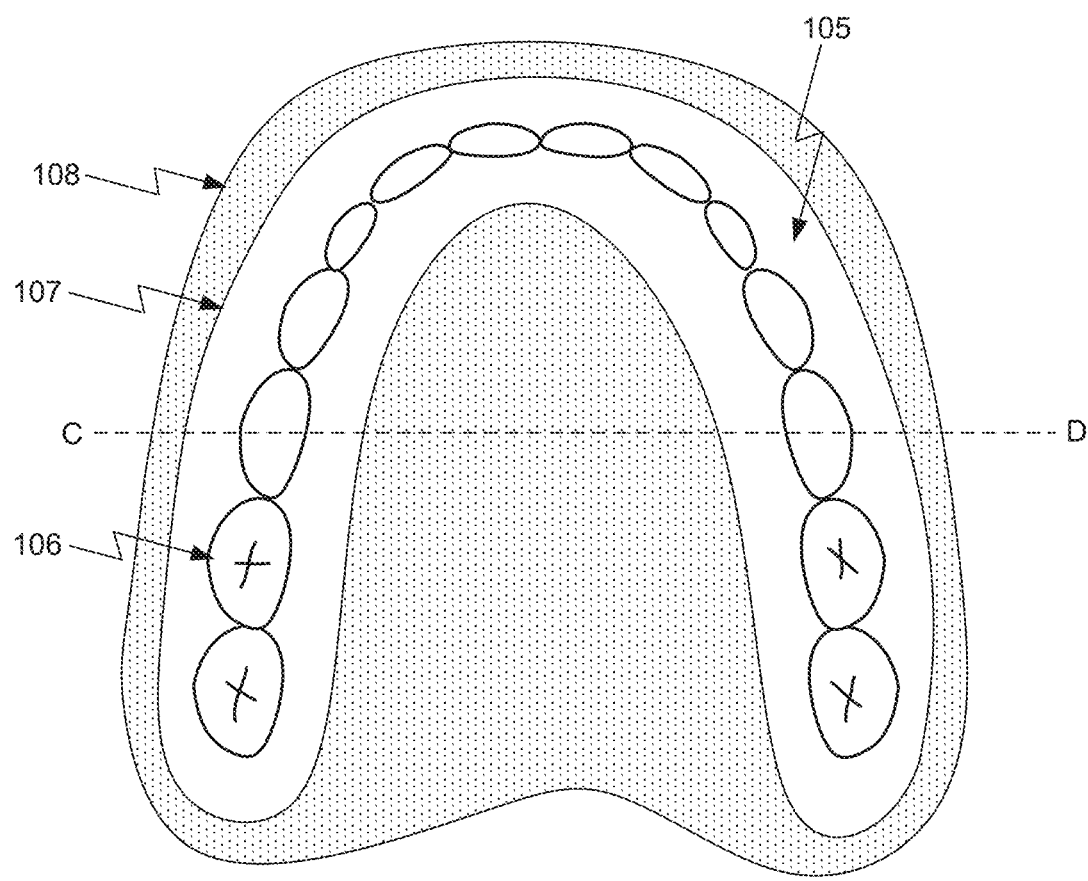

FIG. 1C shows a schematic of a mandibular denture 105, i.e. a denture for the patient's lower jaw viewed from the patient's occlusal plane. The artificial teeth 106 of the mandibular denture 105 are secured in the denture base 107 which contacts the patient's gums 108 in the lower jaw. The illustrated denture is for a completely edentulous lower jaw and the artificial teeth 101 define the occlusion in collaboration with antagonist teeth of the upper jaw, i.e. artificial teeth of a maxillary denture or natural teeth of the upper jaw.

Figure 1D:
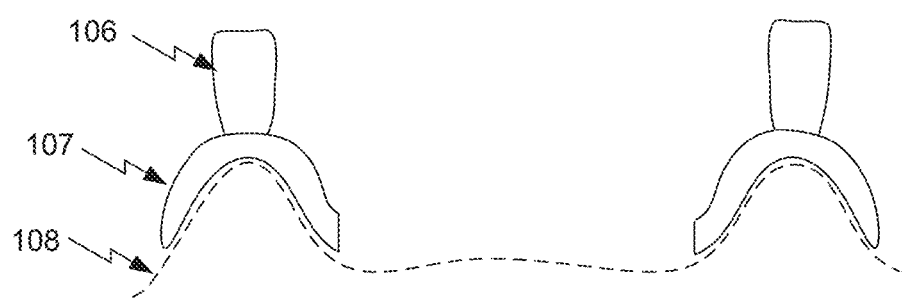

FIG. 1B shows a cross section of the denture/gum tissue at the dotted line A-B of FIG. 1A as seen from the patient's front. FIG. 1D shows a cross section of the mandibular denture and dental tissue at the dotted line C-D as seen from the patient's front. The mandibular denture is shaped to follow the patient's arch and hence has an open area where the soft tissue of the gum 108 is visible.

FIGS. 1B and 1D illustrate that the dentures 100, 105 cover the gum tissue 103, 108 except at the boundaries of the denture. An intra-oral scanning of the patient with the dentures arranged in the mouth can thus provide geometrical data for the artificial teeth 101, 106 but will not provide any information about the position of the gum tissue at the alveolar ridge of the jaws relative to the occlusal surfaces of the artificial teeth 101, 108 of the dentures 100, 105.

The schematic drawings of FIGS. 2 to 5 illustrate the cross sectional views of the gums, teeth (artificial and/or antagonist teeth), and the dentures corresponding to the cross-sections seen in FIGS. 1B, and 1D.

FIG. 2 illustrates the use of the impression material for a obtaining a correct representation of the patient's gum profile.

Figure 2A:
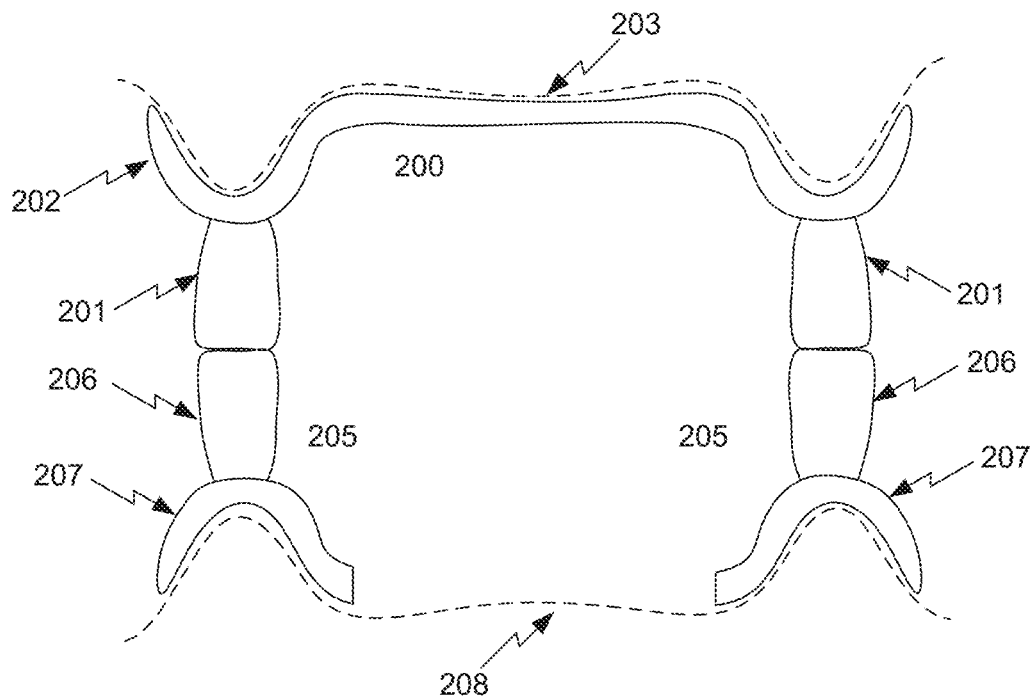
FIGS. 2A-2D illustrate the use of the impression material at the denture.

FIG. 2A illustrates a case where both the patient's upper and lower jaw are completely edentulous and the patient's occlusion plane is defined by the first and second dentures 200, 205. In the bite position the artificial teeth 201 of the first denture 200 engage the artificial teeth 206 of the second denture 205 while the denture bases 202, 207 engages the gum tissue 203, 208 in the upper and lower jaws. Since the gums at the alveolar ridge are hidden under the dentures it is not possible to determine the relative arrangement of the upper and lower jaws in the bite position of the dentures.

Figure 2B:
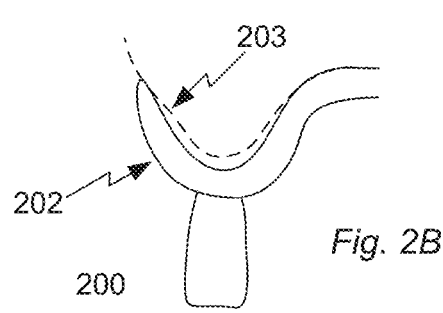

One way of solving this problem is to obtain a so-called bite scan in which the dentures are arranged in occlusion. Such a bite scan provides information relating to the relative arrangement of the artificial teeth of the mandibular and maxillary dentures while these are arranged according to their occlusion. Further the dentures are scanned separately, i.e. not in the mouth, where both the teeth side and the backside (gum-facing part of denture base) are scanned. The relative arrangement of the backsides of the dentures in the bite position can then be determined from the digital 3D representations of the scanned dentures and the bite scan e.g. by aligning the two digital 3D representations with the bite scan which provides that the two digital 3D representations, and hence the backsides of the dentures, are arranged according to the bite position. From an assumption that the backside of the dentures are identical to the corresponding gum surfaces and thus that the geometrical data of the digital 3D representations relating to the backside of the denture expresses the precise shape and position of the gum surfaces the relative arrangement of the gum surfaces in the bite position are then determined. However, as illustrated in FIG. 2B the backside of the denture base 202 and the gum profile 203 at the alveolar ridge does not always coincide over their entire interface. The relatively stiff material of the denture base does not adapt to take the shape of the gum. Accordingly there are regions of the interface where there is a gap between the denture base backside (the gum-facing surface) and the gums such that scanning the backside of the denture 200 does not provide a precise measurement of shape and position of the gum profile relative to the tooth surfaces of the denture. Accordingly aligning the digital 3D representations of the dentures with the digital 3D representation of the bite scan does not provide a precise measurement of the relative arrangement of the gums in the upper and lower jaw in the bite.

Figure 2C:
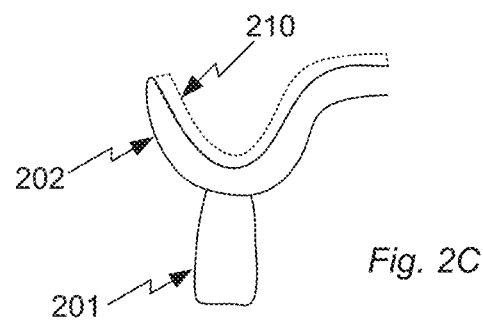
Figure 2D:
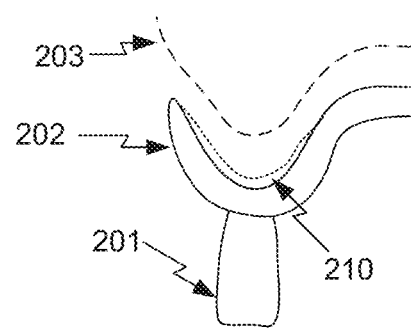

A solution to this problem is illustrated in FIG. 2C where a layer of an impression material 210 is attached to the backside of the denture base 202 before arranging the denture at the patient's gums according to the bite position. The impression material is sufficiently soft to provide that when the denture is arranged at the patient's gum, the impression material takes the form of the gum profile 203, while it still maintains the shape of the gum profile when the denture is removed from the mouth as seen in FIG. 2D. The impression material can be one of the usual impression materials used for acquiring impressions of e.g. a patient's set of teeth, such as elastomers, polysulfides, polyethers and silicones. The impression material provides that when the denture is scanned its backside is shaped precisely as the gum and a precise representation of the gum surfaces and their relative arrangement in the patient's bite position can be obtained based on information from a bite scan.

FIG. 3 illustrates a workflow for determining the relative arrangement of the patient's jaws in a bite position for a case where both the upper and lower jaws are completely edentulous and the occlusion is defined by dentures for upper and lower jaws, i.e. a maxillary and a mandibular denture.

In the example described below, the first and second jaws are the upper and lower jaws, respectfully, without limiting the scope of the application and claims to this combination. Further the order of the steps is not limited by the order described here.

Figure 3A:
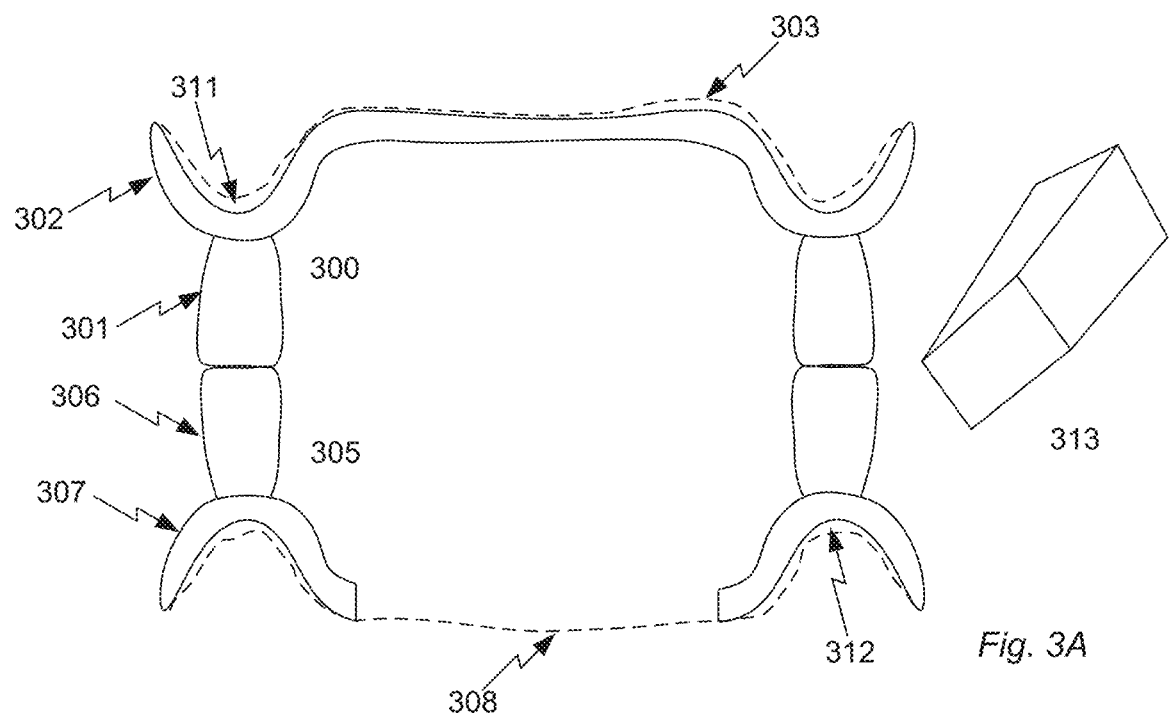
FIGS. 3A-3I illustrate a workflow.

FIG. 3A shows the dentures for the upper and lower jaws arranged according to the patient's bite when wearing the dentures, i.e. when the dentures define the occlusion. The impression material is provided at the backsides of the bases 302, 307 of the upper and lower dentures 300, 305 before these are arranged in the mouth. When the dentures are placed at the patient's gums the impression layer material 311, 312 is takes the shape of the volume bounded by the denture base and the gums such that the gums 303, 308 shape the surface of the impression layer material 311, 312. When the arrangement of the dentures 300, 305 satisfies the operator a so-called bite scan is performed using an intraoral scanner 313 such as the TRIOS scanner from 3shape A/S here symbolized by the tip of the scanner. The 3D scanning provides the second digital 3D representation which comprises geometrical data relating to at least part of the labial/lingual surfaces of the artificial teeth 301, 306 in the two dentures.

Figure 3B:
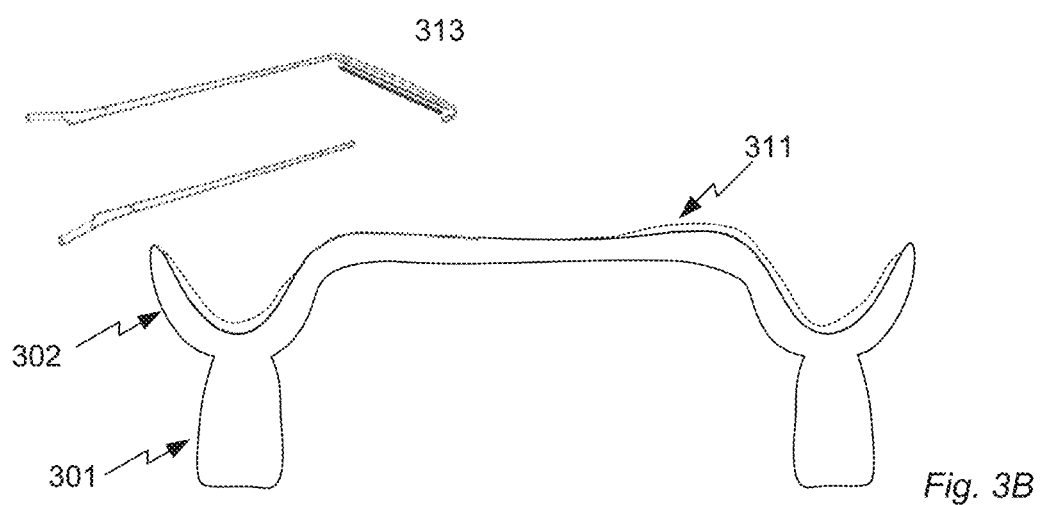

In FIG. 3B the first denture 300 is scanned using the intra-oral scanner 313. The impression material 311 at the backside of the first denture 300 is shaped according to the profile of the gum in the upper jaw. Both the backside of the denture base (i.e. the gum-facing surface with the impression material) 302 and the front side of the denture with the artificial teeth 301 is scanned such that the first digital 3D representation obtained by this scanning comprises geometrical data relating both to the impression material and to the artificial teeth 301. The denture can e.g. be held in the hand by the operator during the scanning.

Figure 3C:
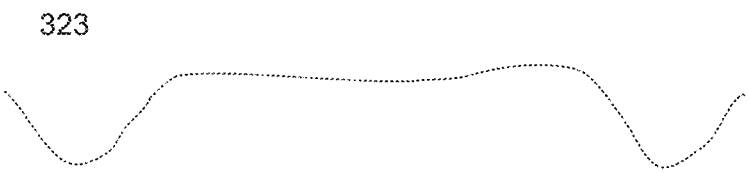

The part of the obtained first digital 3D representation relating to the gum-facing surface of the denture and the impression material situated there can be identified from a visualization of the first digital 3D representation in a user interface. The operator can e.g. use a pointing tool to define a 3D spline which encloses the relevant part of the first digital 3D representation. A third digital 3D representation which expresses the true shape of the gum-surface in the upper jaw can then be derived from the enclosed part of the first digital 3D representation. Such a third digital 3D representation is illustrated in FIG. 3C which shows a cross-section of the third digital 3D representation according to the cross section A-B seen in FIG. 1A.

Figure 3D:
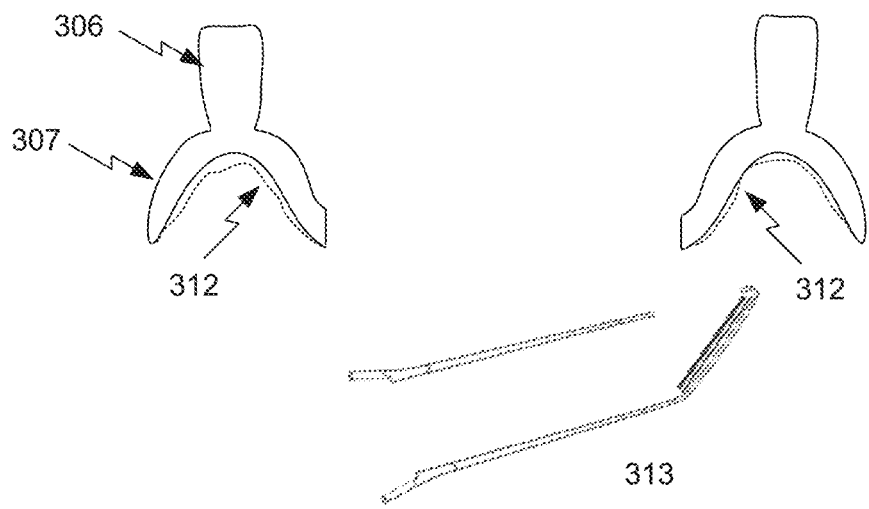

A fourth digital 3D representation is then obtained where the fourth digital 3D representation comprises geometrical data for a surface of the second jaw. When the patient has no teeth in the lower jaw as illustrated in FIG. 3A, the artificial teeth of a second denture arranged at the lower jaw forms the antagonist teeth which together with the artificial teeth of the first denture defines the patient's occlusion. Similar to the steps performed for the first denture in the upper jaw, a second layer of impression material is been arranged at the gum-facing surface of the second denture and the denture is arranged in the mouth according to the bite illustrated in FIG. 3A. When the second denture is removed a fifth digital 3D representation is provided by 3D scanning at least part of the second denture as illustrated in FIG. 3D. The second layer 312 of impression material is arranged at the gum-facing surface of the denture base 307 and is shaped by the gum of the second jaw. The fifth digital 3D representation also has geometrical data for the surface of the artificial teeth 306 of the second denture such that the data can be used for determining the relationship between the bite scan acquired in FIG. 3A and the fifth digital 3D representation.

Figure 3E:

The part of the obtained fifth digital 3D representation relating to the gum-facing surface of the second denture and the impression material situated there can be identified from a visualization of the fifth digital 3D representation in a user interface. The operator can e.g. use a pointing tool to define a 3D spline which encloses the relevant part of the fifth digital 3D representation. Based on the enclosed part of the fifth digital 3D representation the fourth digital 3D representation can be generated. Such a fourth digital 3D representation 324 is illustrated in FIG. 3E which shows a cross-section of the fourth digital 3D representation according to the cross section C-D seen in FIG. 1C.

The relative arrangement of the first digital 3D representation relative to the second digital 3D representation can be determined by mapping or determining transformation matrices for mapping the first and second digital 3D representations into the same coordinate system. The same is the case for the fifth and the second digital 3D representations. In the illustrated example transformation matrices for mapping the first and fifth digital 3D representations into the coordinate system of the second digital 3D representation are determined. These transformation matrices also map the derived third and fourth digital 3D representations into the coordinate system of the second digital 3D representation, whereby the relative arrangement of the upper and lower jaw in the bite position is determined.

Figure 3F:
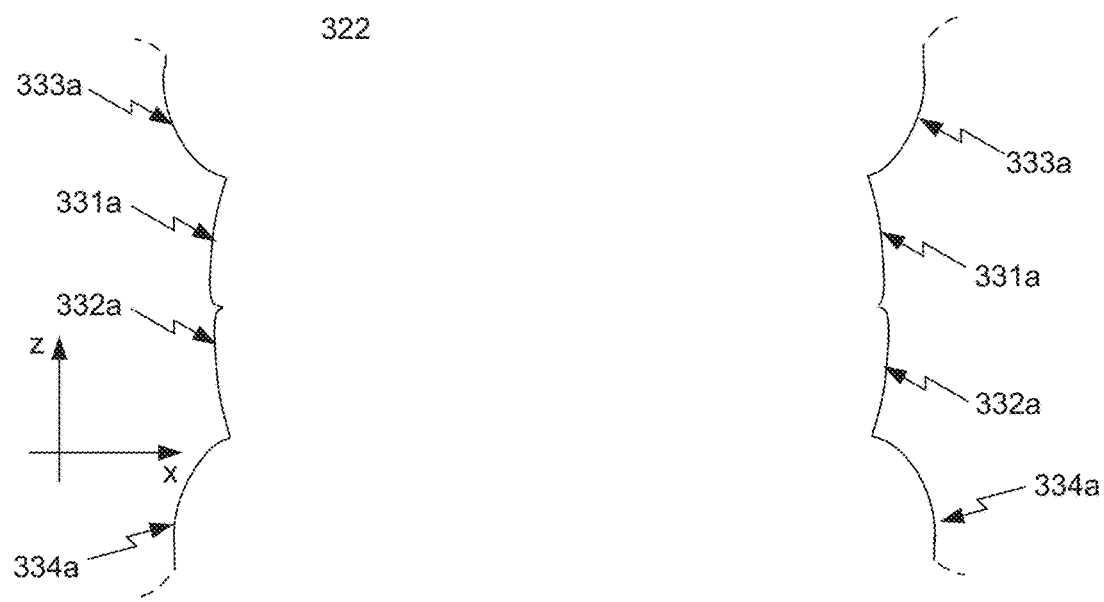

FIG. 3F shows the second digital 3D representation obtained by the bite scan illustrated in FIG. 3A. The second digital 3D representation has geometrical data for the artificial teeth 331a in the first denture and the artificial teeth 332a in the second denture, as well as geometrical data for the bases 333a, 334a of the first and second dentures. As illustrated in the Figure the second digital 3D representation does not contain geometrical data expressing the shape of the gum profile below the dentures in the upper or lower jaw. The second digital 3D representation instead provides valuable information about the relative arrangement of the first and second denture when these are arranged according to the patient's bite.

Figure 3G:
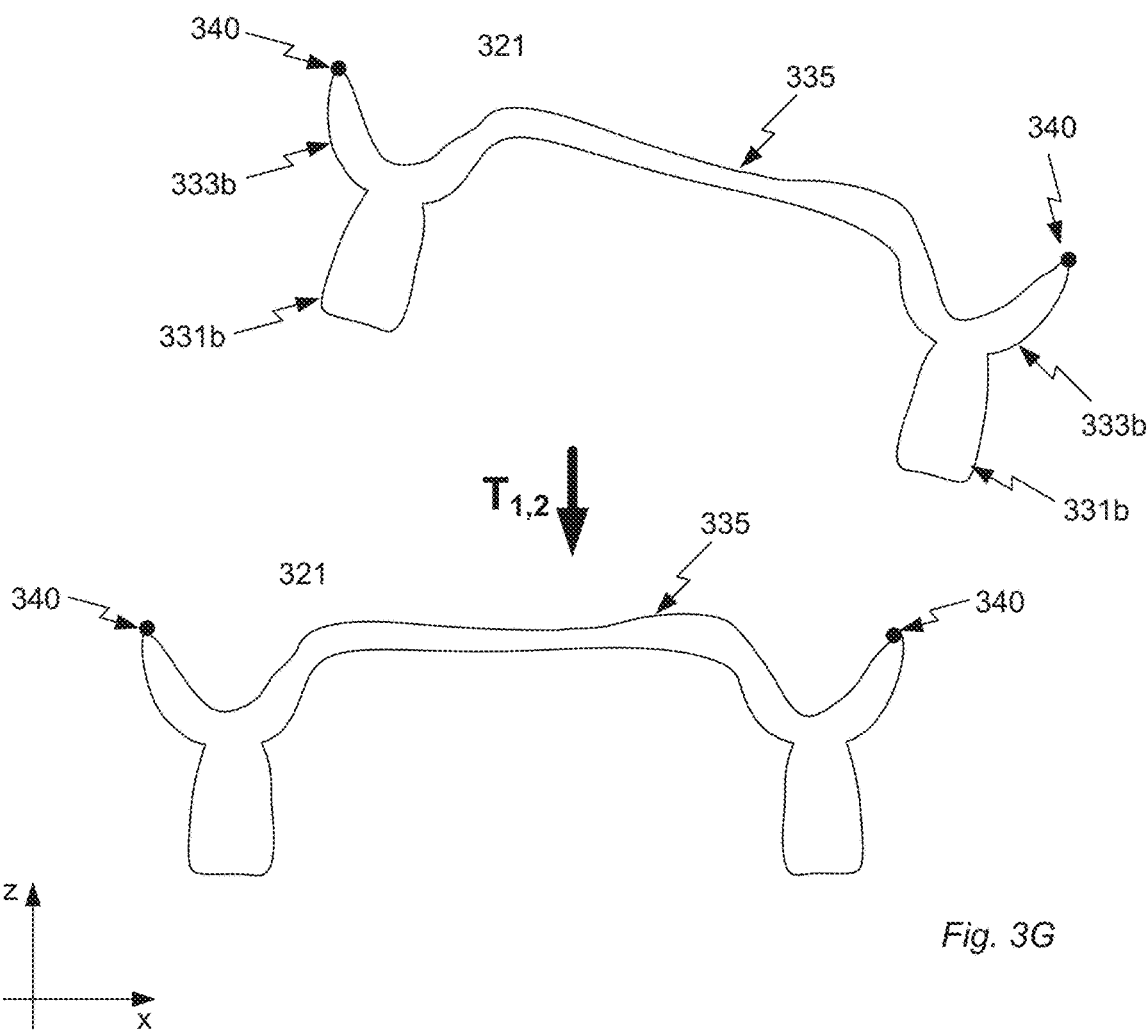

FIG. 3G illustrates the effect of a transformation matrix $T_{1,2}$ configured for mapping the first digital 3D representation into the coordinate system of the second digital 3D representation. The first digital 3D representation 321 expresses the shape of the first denture in the same cross section as seen in FIG. 3B and contains geometrical data for the artificial teeth 331b and the base 333b of the first denture. Further the first digital 3D representation contains geometrical data 335 for the gum-facing surface of the first denture with the gum-facing surface covered in the first layer of impression material shaped according to the true gum-profile of the upper jaw. The gum-facing portion 335 of the first digital 3D representation 321 is bounded by the border 340 which also indicate which parts of the first digital 3D representation are used for deriving the third digital 3D representation expressing the shape of the upper jaw gum. Initially the geometrical data of the first and third digital 3D representations are expressed in the coordinate system of the first digital 3D representation. The transformation matrix $T_{1,2}$ is determined based on the geometrical data of the first and second digital 3D representations corresponding to the same physical surfaces. This is preferably the geometrical data 331a, 331b for the surfaces of the artificial teeth of the first denture and if useful also the data 333a, 333b for the upper/visible parts of the denture base. Often the geometrical data for the artificial teeth are better for alignment of different digital 3D representations. In this example, the first digital 3D representation is displaced and rotated by 20 degrees relative to the coordinate system of the second digital 3D representation. The transformation matrix $T_{1,2}$ is thus configured for compensating for the displacement and the 20 degree rotation such that that the geometrical data of the first digital 3D representation are mapped into the coordinate system of the second digital 3D representation. The transformation matrix $T_{1,2}$ can then be determined using e.g. computer implemented Iterative Closest Point algorithms based on the geometrical data relating to the artificial teeth portions.

After applying the $T_{1,2}$ transformation to the first digital 3D representation all geometrical data of the first digital 3D representation are expressed in the coordinate system of the second digital 3D representation including the data relating to the gum-facing surface. The part of the first digital 3D representation selected to form the third digital 3D representation is hence also expressed in the coordinate system of the bite scan.

Figure 3H:
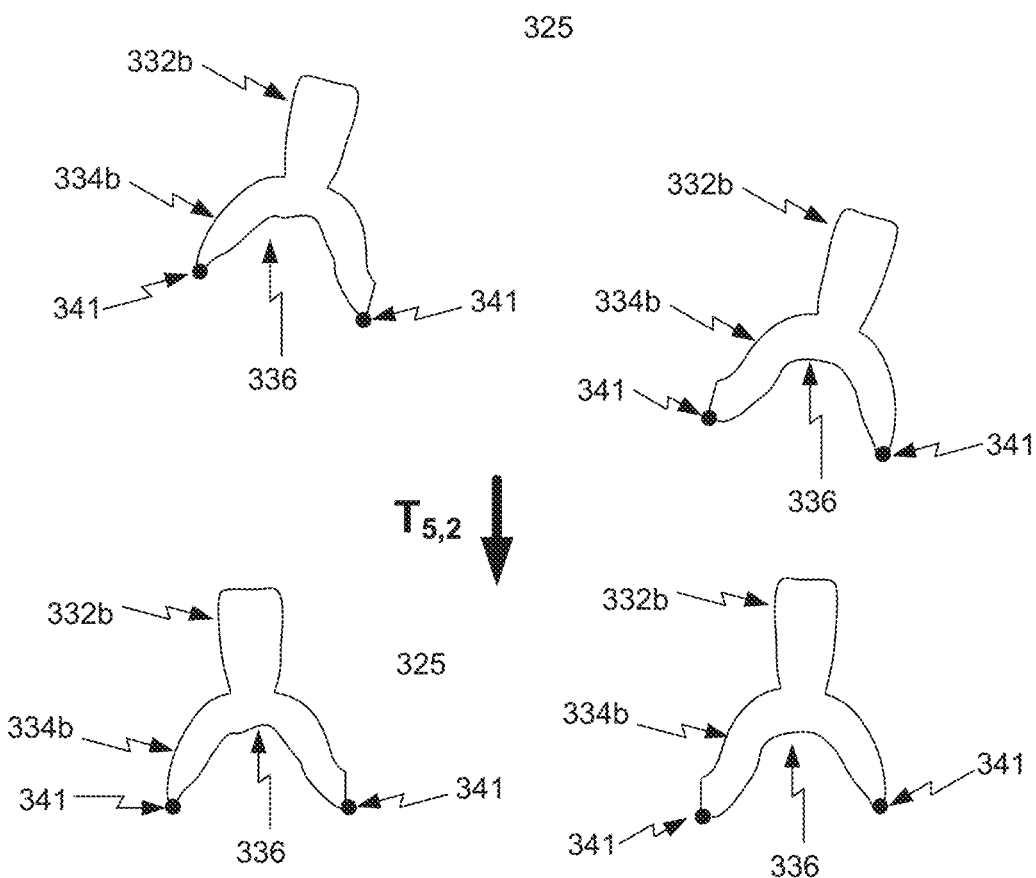

FIG. 3H illustrates the effect of a transformation matrix $T_{5,2}$ configured for mapping the fifth digital 3D representation into the coordinate system of the second digital 3D representation. The fifth digital 3D representation 325 expresses the shape of the second denture in the same cross section as seen in FIG. 3D and contains geometrical data for the artificial teeth 332b and the base 334b of the second denture. Further the fifth digital 3D representation contains geometrical data 336 for the gum-facing surface of the second denture with the gum-facing surface covered in the second layer of impression material shaped according to the true gum-profile of the upper jaw. The gum-facing portion 336 is bounded by the border 341 which also indicate which parts of the fifth digital 3D representation are used for the fourth digital 3D representation expressing the shape of the lower jaw gum. Initially the geometrical data of the fifth and hence the fourth digital 3D representations are expressed in the coordinate system of the fifth digital 3D representation. The transformation matrix $T_{5,2}$ is determined based on the geometrical data 332a, 332b of the fifth and second digital 3D representations corresponding to the artificial teeth of the second denture and brings the geometrical data of the fifth digital 3D representation into the coordinate system of the second digital 3D representation. The transformation matrix $T_{5,2}$ can then be determined using e.g. computer implemented Iterative Closest Point algorithms based on the geometrical data relating to the artificial teeth portions. After applying the $T_{5,2}$ transformation to the second digital 3D representation all geometrical data of the second digital 3D representation are expressed in the coordinate system of the second digital 3D representation including the data relating to the gum-facing surface 336 which forms the fourth digital 3D representation.

Figure 3I:
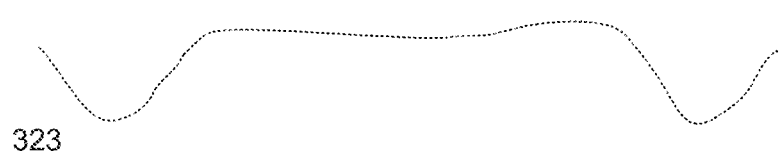
Figure 3I:

Applying first the $T_{1,2}$ and the $T_{5,2}$ transformation matrices on the third 323 and fourth digital 324 3D representations, respectively provides that the geometrical data comprised therein are mapped into the same coordinate system (the coordinate system of the bite scan) as illustrated in FIG. 3I. The relative arrangement of patient's jaws in the bite position is now determined for this edentulous patient.

If the patient has his teeth in the lower jaw, the fourth digital 3D representation can be recorded directly using e.g. an intra oral scanner and will comprise geometrical data expressing the shape of these natural teeth. The relative arrangement of the first denture in the upper jaw and natural teeth of the second jaw in the bite position can then be determined based on the natural teeth geometrical data in the second and fourth digital 3D representations and on the artificial teeth geometrical data in the first and second digital 3D representations. Since the third digital 3D representation relating to the gum surface of the upper jaw is determined from, and hence is uniquely linked to, the first digital 3D representation the third digital 3D representation is aligned with the first digital 3D representation such that when the relative arrangement of the first digital 3D representation and the fourth digital 3D representation is known, the relative arrangement of the third digital 3D representation and the fourth digital 3D representation is also known. In other words, the relative arrangement of the gum surface in the upper jaw and the teeth in the lower jaw during a denture defined bite is determined.

FIG. 4 illustrates how the relative arrangement of the gum surface and a surface of the artificial teeth in a denture can be determined.

Figure 4A:
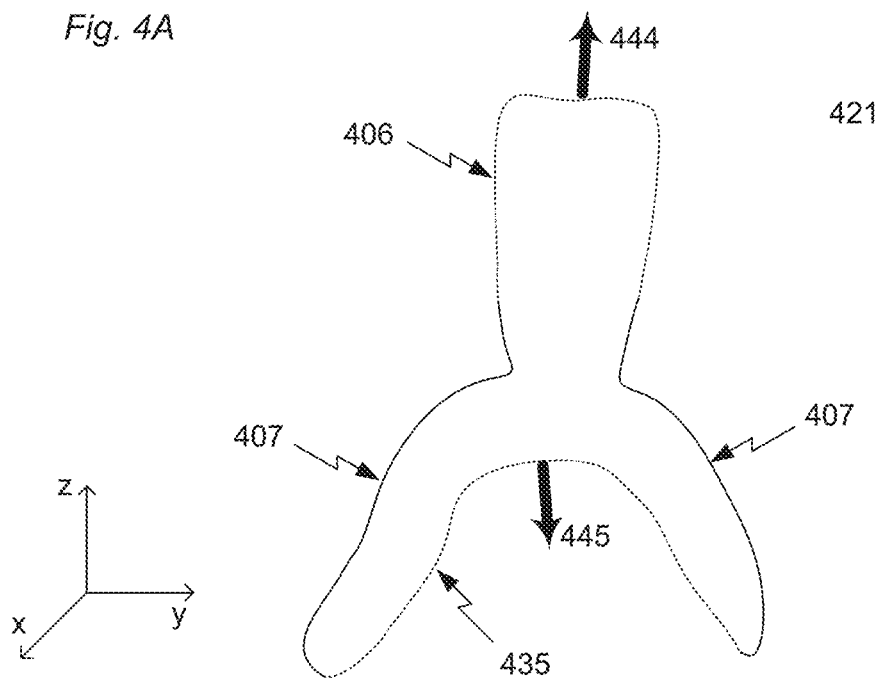
FIGS. 4A-4B illustrate inverting a surface to generate a digital 3D representation.

FIG. 4A shows an illustration of a cross section of a digital 3D representation 421 comprising geometrical data expressing the shape of a portion of an artificial denture tooth 406 (dotted line), for the denture base 407 (solid line) and for a layer of an impression material 435 (dotted line) arranged on the gum-facing surface of the denture base. A 3D spline tool can be used to identify the portion of the digital 3D representation which relates to the selected portion of the artificial tooth. Likewise, the gum-facing portion of the digital 3D representation 421 can be identified by an operator using such a 3D spline tool. The normal vectors 444, 445 of the digital 3D representation points away from the object it represents, i.e. the scanned denture, as seen in FIG. 4A. The layer of impression material is shaped according to the gum of the alveolar ridge such that the shape of the gum surface and its position relative to e.g. the occlusal surface of the artificial tooth can be derived from the digital 3D representation. If the impression material has a color different from that of the denture base, e.g. green such as the soft 3M™ ESPE™ Monophase Polyether impression material, and the digital 3D representation comprises color data, the portion relating to the gum-facing surface can also be determined based on this color information. The denture base may actually in some areas be in contact with the gum surfaces such that there is no impression material in these areas. A computer implemented hole-closing algorithm can then be applied to correct for these holes.

In the illustrated example the selected portion includes the occlusal surface of the artificial tooth which is often advantageous since it is this surface which engages antagonist teeth in the patient's bite and this surface relative to the gums is valuable information when designing e.g. a new denture for the patient. Also the selected portion contains geometrical data for the buccal surface of the artificial tooth which can be advantageous is the portion at some point will be aligned with a bite scan for the patient.

The impression material coated gum-facing surface of the denture base is a negative of the gum-surface and the identified portion 435 of the digital 3D representation 421 relating to the gum-facing surface at the backside of the denture base accordingly provides a negative representation of the gum surface. When a digital 3D representation for the gum surface 448 is derived from the denture digital 3D representation 421 the surface defined by the geometrical data of the identified portion 435 must hence be inverted to provide that the direction of the normal vector 446 of the gum surface digital 3D representation 448 is correct and this digital 3D representation is a positive of the gum surface.

Figure 4B:
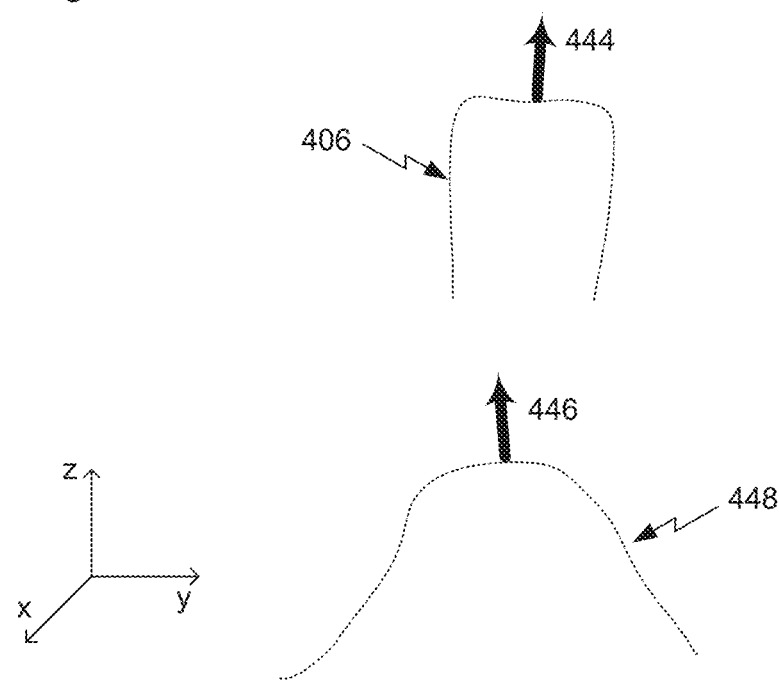

Since the gum surface digital 3D representation 448 is derived from a portion of the denture digital 3D representation 421, the gum surface digital 3D representation 448 is expressed in the same coordinate system as the other portions of the denture digital 3D representation 421. In particular the gum surface digital 3D representation 448 is expressed in the same coordinate system as the geometrical data of the denture digital 3D representation 421 expressing the shape of the selected part of the artificial denture tooth 406. The relative arrangement of selected surface of the artificial teeth and the surface of the gum which the denture rests on has thus been determined. FIG. 4B shows cross sections of part of the geometrical data for the artificial tooth 406 and the geometrical data of the gum surface digital 3D representation 448 with corresponding normal vectors 444, 446.

One workflow for determining the relative arrangement of artificial teeth of a denture and the gum surface at the patient's alveolar ridge where the denture is arranged is described here.

If the patient already has a denture, e.g. for the lower jaw, a layer of an impression material is arranged on the backside of the denture base, i.e. the gum-facing surface of the denture base. The impression material can be selected from the impression materials normally used in dental practices for taking impressions of teeth such as 3M™ ESPE™ Monophase Polyether impression material. The denture is then arranged at the corresponding jaw according to the patient's occlusion while wearing the denture, such that the layer of impression material is shaped according to the alveolar ridge of the jaw. The denture is removed from the patient's mouth and 3D scanned using e.g. a desktop scanner such as the 3Shape D2000 scanner or a handheld scanner such as the 3shape TRIOS intra oral scanner. Both the artificial teeth and the denture backside are scanned such that the obtained digital 3D representation has geometrical data for the artificial teeth of the denture and for the impression material arranged on the gum-facing surface of the denture base. The digital 3D representation is visualized in a user interface displayed e.g. on a computer screen and the artificial tooth surface and the gum surface are identified using a 3D spline tool selecting the relevant portions of the digital 3D representation. The layer of impression material is shaped by the gum surface in the alveolar ridge, however as a negative of the gum surface. The surface formed by the selected geometrical data of the digital 3D representation is thus inverted such that a positive representation of the gum surface is provided. Given that the digital 3D representation contains both the geometrical data for the artificial teeth and the denture back side with the gum shaped impression material the relative arrangement of the artificial tooth surfaces and the gum is thus determined.

FIG. 5 illustrates design of a drill guide body.

FIG. 5A shows a cross section of a denture for the patient's lower jaw is illustrated. The cross section relates to the left part of the jaw and the patient's medial plane is thus to the right of this figure. The denture has artificial teeth 506 and a denture base 507 on which fiducial markers 550 are arranged. On the backside of the denture a layer of impression material 512 is arranged where the impression material is shaped by the patient's gum surface in the alveolar ridge of the lower jaw. When 3D scanning the denture the resulting digital 3D representation comprises data for the artificial teeth, the fiducial markers and the gum-facing surface at the backside of the denture. The digital 3D representation provides a spatial correlation between the markers and the artificial teeth and gum surface.

FIG. 5B shows the data obtained by an X-ray scanning of the patient with the denture arranged in occlusion with teeth of the upper jaw. The fiducial markers are made of a radiopaque material such that these are seen in the X-ray scan together with the jaw bone whereby a spatial correlation between the markers and the jaw bone is provided.

In FIG. 5C the digital 3D representation providing a representation of the denture surface and the X-ray are aligned utilizing that data for the radiopaque fiducial markers 550 are found on both data sets. The relative arrangement of the bone structure 551 and the artificial teeth 506 of the lower jaw is then determined. The gum surface 503 is also indicated to easy the interpretation of the figure.

Figure 5D:
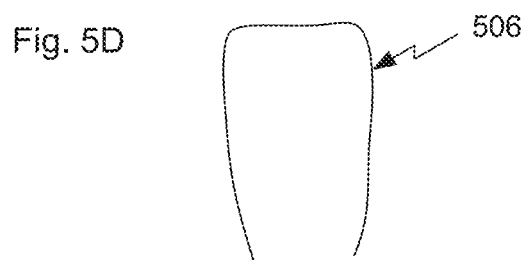
Figure 5E:
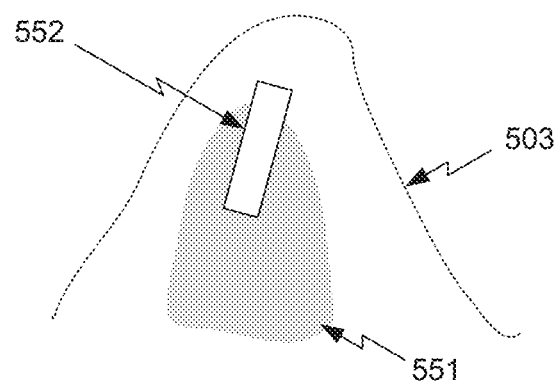
Figure 5E:
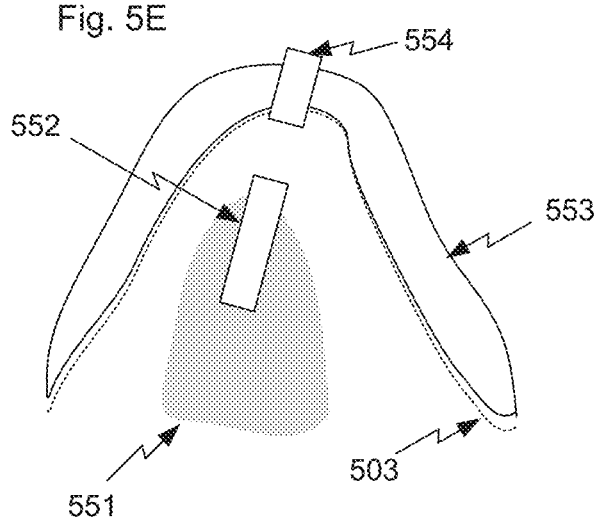

FIG. 5D shows the aligned data for the bone structure 551 and the artificial tooth 506. The patient is getting a new implant supported denture and the appropriate position of the implant in the jaw bone is determined based on the relative position of the jaw bone and the artificial teeth in the target setup which here is identical to the current setup. The planned position of the implant 552 is slightly inclined away from the medial plane of the patient such that a connection (not shown in figure) for the denture to the implant can have a direction substantially aligned with the longitudinal axis of the implant 552.

Figure 5F:
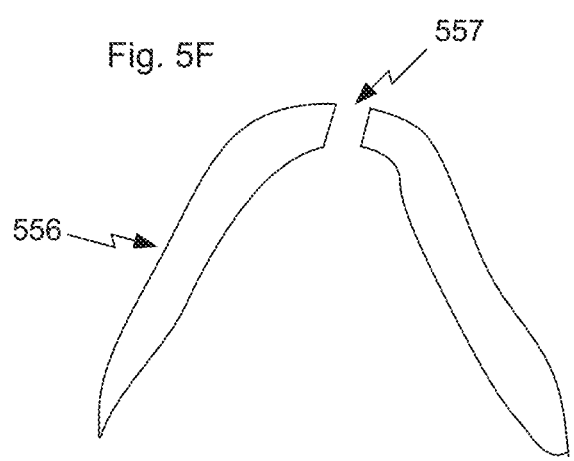

A drill guide body 553 is generated from the geometrical data of the digital 3D representation relating to the impression material and the denture base such that the drill guide body precisely fits the patent's gum surface. The artificial tooth part of the digital 3D representation is replaced by a surface which follows the denture base surface to create a smooth upper surface for the drill guide body 553. A CAD model 554 of a guide tube insert is arranged parallel with the implant 552 and is subtracted from the drill guide body. When this has been repeated for all the implants, the drill guide body design is transferred to a direct digital manufacture machine, such as a 3D printer or a milling machine, and the drill guide body is produced. The manufactured drill guide body 556 is seen in FIG. 5F with the opening 557 provided for the guide tube insert. Different guide tubes can be inserted into the defined opening.

Figure 6:
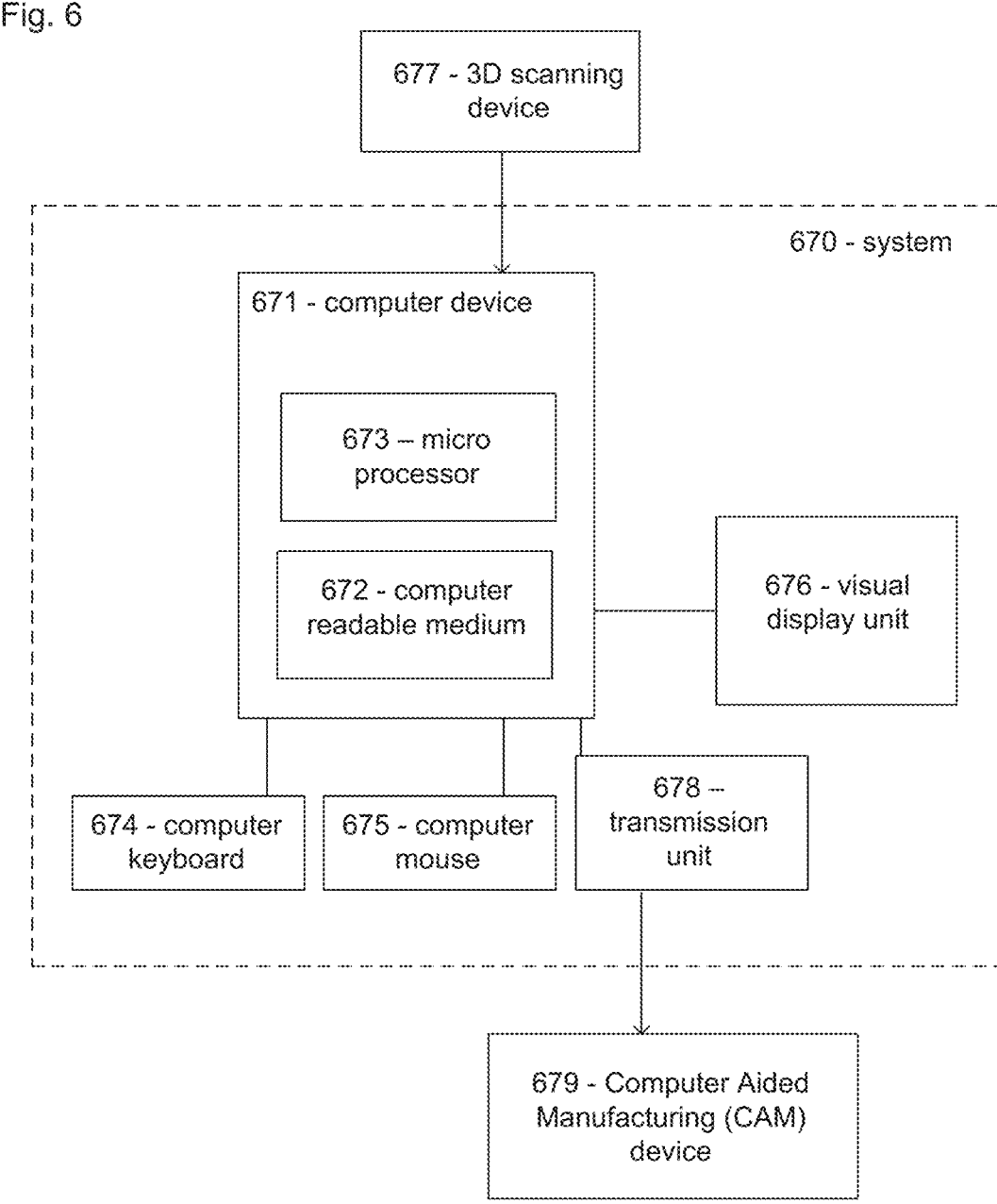
FIG. 6 illustrates a system.

FIG. 6 shows a schematic of a system according to an embodiment of the invention. The system 670 comprises a computer device 671 comprising a computer readable medium 672 and a microprocessor 673. The computer readable medium 672 is encoded with algorithms for implementing the disclosed method, such as algorithms for aligning digital 3D representations when these are loaded into the microprocessor 673. The system further comprises a visual display unit 676, such as a computer screen, and a computer keyboard 674 and a computer mouse 675 for entering data and activating virtual buttons visualized on the visual display unit 676.

The computer device 671 is capable of obtaining digital representations recorded using a 3D scanner 677, such as the TRIOS intra-oral scanner manufactured by 3shape TRIOS A/S, or capable of receiving scan data from such a 3D scanning device and forming a digital 3D representation based on such scan data. The received or formed digital 3D representation can be stored in the computer readable medium 672 and loaded therefrom into the microprocessor 673.

The system 670 is configured for allowing an operator to select the different digital 3D representations and to visualize these in a user interface depicted on the visual display unit 676. The alignment of the digital 3D representation can thus be verified by the operator who also can select which portion of the first digital 3D representation relates to the gum-facing surface using e.g. the computer mouse 675 or the computer keyboard 674. During the workflow for performing the disclosed method one or more options can be presented to the operator, such as whether to accept or manually improve the alignment derived by the microprocessor. The options can be presented in the user interface.

The system comprises a unit 678 for transmitting e.g. a generated digital drill guide design to a computer aided manufacturing (CAM) device 679 for manufacturing a drill guide body or to another computer system e.g. located at a milling center where the drill guide is manufactured. The unit for transmitting can be a wired or a wireless connection.

The 3D scanning using the 3D scanning device 677 can be performed at a dentist while the relative arrangement of the jaws is determined at a dental laboratory. In such cases the digital 3D representations can be provided via an internet connection between the dentist and the dental laboratory.

FIG. 7 shows a schematic of a user interface according to an embodiment of the invention.

The user interface 780 has a first part 781 in which a cross section of a digital 3D representation 762 of the denture is visualized. The portion of the digital 3D representation relating to the gum-facing surface can be selected using a 3D spline enclosing the relevant geometrical data of the digital 3D representation. The 3D spline can be generated from using e.g. a computer mouse. Computer implemented algorithms can then be used to invert the surface such that gum surface digital 3D representation is generated which gives a positive representation of the gum surface.

The second part 783 of the user interface comprises a data entering sections 785, 786 for entering various data relating to the method such as for loading the different digital 3D representations into the user interface. A virtual push button 784 is configured activating computer implemented algorithms e.g. for generating the gum surface digital 3D representation or for determining the relative arrangement of the first and second jaws in the bite position based on the geometrical data of the loaded digital 3D representations when the button is activated. The user interface can be visualized on a visual display unit, such as a computer screen being part of a system configured for implementing the method according to the present invention.

SELECTED FIGURE REFERENCE NUMBERS

In the Figures the reference numbers are provided in the format according to XYY where "X" is a Figure number indicator showing in which Figure the reference is used and YY is the item number indicator according to the following list.

00 maxillary denture
01 artificial teeth of maxillary denture
02 base of maxillary denture
03 gum of upper jaw
05 mandibular denture
06 artificial teeth of mandibular denture
07 base of maxillary denture
08 gum of upper jaw
10 layer of impression material
11 impression material at backside of first denture
12 impression material at backside of second denture
13 intra-oral scanner
21 first digital 3D representation—of first denture with impression material
22 second digital 3D representation—bite scan
23 third digital 3D representation—of surface of the first jaw
24 fourth digital 3D representation—of surface of the second jaw
25 fifth digital 3D representation—of second denture with impression material
31 geometric data for artificial teeth in first denture
32 geometric data for artificial teeth in second denture
33 geometric data for base of first denture
34 geometric data for base of second denture
35 geometric data for gum-facing surface of first denture 36 geometric data for gum-facing surface of second denture
40 boundary of gum-facing surface of first denture
41 boundary of gum-facing surface of second denture
44 normal vector of first digital 3D representation at artificial tooth surface
45 normal vector of first digital 3D representation at denture base.
46 normal vector of third digital 3D representation.
48 geometric data for gum surface.
50 fiducial markers
51 bone structure
52 implant in planned position
53 denture base body
54 CAD model of guide tube insert
56 physical drill guide body
57 opening for guide tube insert
70 system
71 computer device
72 computer readable medium
73 microprocessor
74 computer keyboard
75 computer mouse
76 display
77 3D scanner
78 transmitting unit
79 CAM production device
80, 81, 83 user interface
82 virtual tool
84 virtual push button
85, 86 data entering sections Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The invention claimed is:

1. A method for determining a relative arrangement of a patient's first and second jaws in a bite position at least partly defined by a first denture so that a relative spacing can be maintained between the patient's first and second jaws when using a new denture for the first jaw, the method comprising:

obtaining a first digital 3D representation of the first denture for the first jaw, where the first digital 3D representation comprises geometrical data for artificial teeth of the first denture and for a first surface of a base of the first denture, which surface is configured to face a gum of the first jaw, where a first layer of impression material shaped according to a surface of the gum of the first jaw is arranged at the first surface of the base of the first denture, the first layer of impression material having a shape of the surface of the gum of the first jaw by having previously placed the first denture with the first layer of impression material at the surface of the gum of the first jaw;

obtaining a second digital 3D representation comprising geometrical data for the artificial teeth of the first denture and geometrical data for antagonist teeth in the second jaw, where the artificial teeth of the first denture and the antagonist teeth are arranged according to occlusion of the patient;

mapping the first digital 3D representation into a coordinate system of the second digital 3D representation;

deriving from the first digital 3D representation and the second 3D representation a third digital 3D representation comprising geometrical data for the surface of the gum of the first jaw in the coordinate system of the second digital representation;

obtaining a fourth digital 3D representation comprising geometrical data for the second jaw; and mapping the fourth digital 3D representation into the coordinate system of the second digital 3D representation, and using the geometrical data of the mapped first, second, and fourth digital 3D representations and the third digital 3D representation to determine the relative spacing of the surface of the gum of the first jaw and the antagonist teeth when using a new denture for the first jaw.

2. The method according to claim 1, wherein the antagonist teeth comprises natural teeth of the second jaw and at least part of the geometrical data comprised in the fourth digital 3D representation relates to a surface of the natural teeth of the second jaw, and where the relative arrangement of the gum of the first jaw and the natural teeth of the second jaw is determined at least partly by establishing a spatial correlation between the third and fourth digital 3D representations.

3. The method according to claim 1, wherein the antagonist teeth comprises artificial teeth of a second denture for the patient's second jaw and a second layer of impression material shaped according to the gum of the second jaw is arranged at the gum-facing surface of the base of the second denture, and where the method comprises obtaining a fifth digital 3D representation provided by 3D scanning at least part of the second denture such that the fifth digital 3D representation comprises geometrical data for the surface of the artificial teeth of the second denture and for the gum-facing surface with the second layer of impression material.

4. The method according to claim 3, wherein the fourth digital 3D representation is derived from a part of the geometrical data of the fifth digital 3D representation relating to the gum-facing surface of the second denture with the second layer of impression material, and where the relative arrangement of the gum of the first jaw and the gum of the second jaw is determined at least partly by establishing a spatial correlation between the third and fourth digital 3D representations.

5. The method according to claim 1, wherein determining the relative arrangement comprises deriving one or more transformations for mapping the third and fourth digital 3D representations into the same coordinate system.

6. The method according to claim 5, wherein said one or more transformations provide a mapping of the first and second digital 3D representations into the same coordinate system at least partly based on the geometrical data for the artificial teeth in the first digital 3D representation and the corresponding part of the geometrical data of the second digital 3D representation.

7. The method according to claim 5, wherein said one or more transformations provide a mapping of the second and fifth digital 3D representations into the same coordinate system at least partly based on the geometrical data for the artificial teeth in the fifth digital 3D representation and the corresponding part of the geometrical data of the second digital 3D representation.

8. The method according to claim 5, wherein said one or more transformations provide a mapping of the second and fourth digital 3D representations into the same coordinate system at least partly based on the geometrical data for the natural teeth of the second jaw in the fourth digital 3D representation and the corresponding part of the geometrical data of the second digital 3D representation.

9. The method according to claim 1, wherein the third or fourth digital 3D representation comprises geometrical data for the alveolar ridge and/or the palatine rugae of the patient's upper jaw, or wherein a sixth digital 3D representation comprising geometrical data for the alveolar ridge and/or the palatine rugae is obtained and the method comprises determining one or more transformations for mapping the sixth digital 3D representation into the coordinate system of the first, second or fourth digital 3D representation.

10. The method according to claim 1, wherein a digital drill guide design is generated for the first jaw based on the first digital 3D representation and an obtained x-ray image describing the bone of the first jaw, wherein the method comprises generating a digital drill guide body from a portion of the first digital 3D representation comprising geometrical data for the gum-facing surface with the first layer of impression material and subtracting from the digital drill guide body one or more CAD models of inserts for guide tubes shaped to assist a drill in drilling implant holes into the patient's jaw.

11. The method according to claim 1, wherein deriving the third digital 3D representation comprises selecting the portion of the geometrical data of the first digital 3D representation relating to the gum-facing surface of the denture base and inverting the surface normal of the surface defined by the selected portion.

\* \* \* \* \*